(12) United States Patent
Cook et al.

(10) Patent No.: US 6,783,931 B1
(45) Date of Patent: Aug. 31, 2004

(54) AMINE-DERIVATIZED NUCLEOSIDES AND OLIGONUCLEOSIDES

(75) Inventors: Phillip Dan Cook, Carlsbad, CA (US); Muthiah Manoharan, Carlsbad, CA (US); Charles J. Guinosso, Vista, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 1826 days.

(21) Appl. No.: 08/117,363

(22) Filed: Sep. 3, 1993

Related U.S. Application Data

(63) Continuation-in-part of application No. PCT/US92/09196, filed on Oct. 23, 1992, which is a continuation-in-part of application No. 07/782,374, filed on Oct. 24, 1991, now abandoned, which is a continuation-in-part of application No. PCT/US91/00243, filed on Jan. 1, 1991, which is a continuation-in-part of application No. 07/566,977, filed on Aug. 13, 1990, now abandoned, and a continuation-in-part of application No. 07/463,358, filed on Jan. 11, 1990, now abandoned.

(30) Foreign Application Priority Data

Oct. 23, 1992 (WO) .............................. PCT/US92/09196

(51) Int. Cl.$^7$ .......................... C12Q 1/68; C12P 19/34; C07H 21/02; C07H 21/04; C07H 19/00
(52) U.S. Cl. .......................... 435/6; 435/7.1; 435/91.1; 435/91.2; 536/22.1; 536/23.1; 536/24.3; 536/24.31; 536/24.32; 536/24.33; 536/24.5; 536/25.32
(58) Field of Search ............................. 536/24.5, 25.32; 435/6

(56) References Cited

U.S. PATENT DOCUMENTS

| | | | |
|---|---|---|---|
| 3,687,808 A | | 8/1972 | Merigan, Jr. et al. .......... 195/28 |
| 4,743,535 A | * | 5/1988 | Carrico ........................... 435/6 |
| 4,910,300 A | * | 3/1990 | Urdea et al. ................. 536/287 |
| 4,958,013 A | | 9/1990 | Letsinger ...................... 536/27 |
| 5,466,786 A | | 11/1995 | Buhr et al. ............... 536/26.26 |

FOREIGN PATENT DOCUMENTS

| WO | WO 91/14696 | | 11/1991 | |
|---|---|---|---|---|
| WO | WO 92/05186 | * | 4/1993 | ........... C07H/15/12 |

OTHER PUBLICATIONS

Stein et al. Science 261:1004–1012, Aug. 20, 1993.*
Solomons, Organic Chemistry, p. 818–819, pub. by John Wiley & Sons, 1980.*
Englisch, et al., "Chemically Modified Oligonucleotides as Probes and Inhibitors" *Angew. Chem. Ed. Eng. 1991*, 30, 613.
Manoharan, et al., "Novel Functionalization of the Sugar Moiety of Nucleic Acids for Multiple Labeling in the Minor Grove" *Tetrahedron Letters* 1991, 32, 7171.

Goodchild, "Conjugates of Oligonucleotides and Modified Oligonucleotides: A Reviw of Their Synthesis and Properties" *Bioconjugate Chemistry* 1990, 1, 165.

Monoharan, et al., "Chemical Modifications to Improve Uptake and Bioavailability of Antisense Oligonculeotides" *Database Embase Elsevier Science Publishers* 1992 660, 306 (abstract).

Asseline et al., "Nucleic acid–binding molecules with high affinity and base sequence specificity: Intercalating agents covalently linked to oligodeoxynucleotides," *Proc. Natl. Acad. Sci. USA* 81:3297–3301, 1984.

Beaucage et al., "Advances in the Synthesis of Oligonucleotides by the Phosphoramidite Approach," *Tetrahedron* 48:2223–2311, 1992.

Betebenner et al., "Hepatobiliary Delivery of Polyaminopolycarboxylate Chelates: Synthesis and Characterization of a Cholic Acid Conjugate of EDTA and Biodistribution and Imaging Studies with Its Indium–111 Chelate," *Bioconjugate Chem.*, 2:117–123, 1991.

Chollet, A. "Selective Attachment of Oligonucleotides to Interleukin–1 beta and Targeted Delivery to Cells," *Nucleosides & Nucleotides*, 9:957–966, 1990.

Corey et al., "Generation of a Hybrid Sequence–Specific Single–Stranded Deoxyribonuclease," *Science*, 238:1401–1403, 1987.

Corey et al., "Sequence–Selective Hydrolysis of Duplex DNA by an Oligonucleotide–Directed Nuclease," *J. Am. Chem. Soc.*, 111:8523–8525, 1989.

Damha et. al., "An improved procedure for derivatization of controlled–pore glass beads for solid–phase oligonucleotide synthesis," *Nucl. Acids Res.* 18:3813–3821, 1990.

Delgardo et al., "The Uses and Properties of PEG–Linked Proteins," *Critical Reviews in Therapeutic Drug Carrier Systems*, 9:249–304, 1992.

Dreyer et al., Sequence–specific cleavage of single–stranded DNA: oligodoexynucleotide–EDTA.Fe (II), *Proc. Natl. Acad. Sci. USA*, 82:968–972, 1985.

Guerra et al., "Synthetic 6–Glucosyl Phospholipid as a Drug Transport System," *Tetrahedron Letters*, 28:3581–3584, 1987.

(List continued on next page.)

*Primary Examiner*—Jeffrey Siew
(74) *Attorney, Agent, or Firm*—Woodcock Washburn LLP

(57) ABSTRACT

Nucleosides and oligonucleosides functionalized to include alkylamino functionality, and derivatives thereof. In certain embodiments, the compounds of the invention further include steriods, reporter molecules, reporter enzymes, lipophilic molecules, peptides or proteins attached to the nucleosided through the alkylamino group.

29 Claims, No Drawings

OTHER PUBLICATIONS

Haralambidis et al., "Preparation of base–modified nucleosides suitable for non–redioactive label attachment and their incorporation into synthetic oligodeoxyribonucleotides," *Nucleic Acid Research*, 15: 4857–4877, 1987.

Haralambidis et al., "The Solid Phase Synthesis of Oligonucleotides Containing a 3'–Peptide Moiety," *Tetrahedron Letters*, 28:5199–5202, 1987.

Iyer et al., "3H–1,2–Benzodithiole–3–one 1,1–Dioxide as an Improved Sulfurizing Reagent in the Solid–Phase Synthesis of Oligodeoxyribonucleoside Phosphorothioates," *J. Am. Chem. Soc.*, 112:1253–1254, 1990.

Juby et al., "Facile Preparation of 3'Oligonucleotide–Peptide Conjugates," *Tetrahedron Letters*, 32: 879–882, 1991.

Krieg et al., "Uptake of Oligodeoxyribonucleotides by Lymphoid Cells Is Heterogeneous and Inducible," *Antisense Research and Development*, 1:161–171, 1991.

Lemaitre et al., "Specific antiviral activity of a poly(L–lysine)–conjugated oligodeoxyribonucleotide sequence complementary to vesicular stomatitis virus N protein mRNA initiation site," *Proc. Natl. Acad. Sci. USA*, 84:648–652, 1987.

Leonetti et al., "Biological Activity of Oligonucleotide–Poly(L–lysine) Conjugates: Mechanism of Cell Uptake," *Bioconjugate Chem.*, 1:149–153, 1990.

Letsinger et al., "Cholesteryl–conjugated oligonucleotides: Synthesis, properties, and activity as inhibitors of replication of human immunodeficiency virus in cell culture," *Proc. Natl. Acad. Sci. USA*, 86:6553–6556, 1989.

Miller et al., "A New Approach to chemotherapy based on molecular biology and nucleic acid chemistry: Matagen (masking tape for gen expression)," *Anti–Cancer Drug Design*, 2:117–128, 1987.

Nelson et al., "Bifunctional oligonucleotide probes synthesized using a novel CPG support are able to detect single base pair mutants," *Nuc. Acids Res.*, 17:7187–7194, 1989.

Ouchi et al., "Synthesis and Antitumor Activity of Poly(Ethylene Glycol)s Linked to 5–Fluorouracil Via a Urethane of Urea Bond," *Drug Design and Discovery*, 9:93–105, 1992.

Ramirez et al., "Nucleotidophospholipids: Oligonucleotide Derivatives with membrane–Recognition Groups," *J. Am. Chem. Soc.*, 104:5483–5486, 1982.

Ravasio et al., "Selective Hydrogenations Promoted by Copper Catalysts. 1. Chemoselectivity, Regioselectivity, and Stereoselectivity in the Hydrogenation of 3–Substituted Steroids," *J. Org. Chem.*, 56:4329–4333, 1991.

Shea et al., "Synthesis, hybridization properties and antiviral activity of lipid–oligodeoxynucleotide conjugates," *Nuc. Acids Res.*, 18:3777–3783, 1990.

Smith–Jones et. al., "Antibody Labeling with Copper–67 Using the Bifunctional Marcrocycle 4–[(1,4,8, 11–Tetraazacyclotetradec–1–yl)methyl]benzoic Acid," *Bioconjugate Chem.*, 2:415–421, 1991.

Telser et al., "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements," *J. Am. Chem. Soc.*, 111:6966–6976, 1989.

Veber et al., "Isonicotinyloxycarbonyl, a Novel Amino Protecting Group for Peptide Synthesis," *J. Org. Chem.* 42:3286–3288, 1977.

Wagner et. al., "Preparation and Synthetic Utility of Some Organotin Derivatives of Nucleosides," *J. Org. Chem.*, 39:24–30, 1974.

Yamana et al., "Synthesis of Oligonucleotide Derivatives with Pyrene Group at Sugar Fragment," *Tetrahedron Lett.*, 32: 6347–6350, 1991.

Yamana et al., "Synthesis and Interactive Properties of an Oligonucleotide with Anthraquinone at the Sugar Fragment," *Bioconjugate Chem.*, 1:319–324, 1990.

Zuckermann et al., "Site–Selective Cleavage of RNA by a Hybrid Enzyme," *J. Am. Chem. Soc.*, 110:1614–1615, 1988.

* cited by examiner

AMINE-DERIVATIZED NUCLEOSIDES AND OLIGONUCLEOSIDES

CROSS REFERENCE TO RELATED APPLICATION

This application is a continuation-in-part of application Ser. No. PCT/US92/09196, filed on Oct. 23, 1992, which is a continuation-in-part of application Ser. No. 07/782,374, filed on Oct. 24, 1991, now abandoned, which is a continuation in part of application Ser. No. PCT/US91/00243, filed Jan. 1, 1991, which is a continuation-in-part of application Ser. No. 07/463,358, filed on Jan. 11, 1990, now abandoned, and of application Ser. No. 07/566,977, filed on Aug. 13, 1990, now abandoned. The entire disclosures of each of these applications, which are assigned to the assignee of this application, are incorporated herein by reference.

FIELD OF THE INVENTION

This application is directed to nucleosides, oligonucleotides and oligonucleosides functionalized to include alkylamino functionality, and derivatives thereof. In certain embodiments, the compounds of the invention further include steroids, reporter molecules, reporter enzymes, lipophilic molecules, peptides or proteins attached to the nucleosides through the alkylamino group.

BACKGROUND OF THE INVENTION

Messenger RNA (mRNA) directs protein synthesis. Antisense methodology is the complementary hybridization of relatively short oligonucleotides to mRNA or DNA such that the normal, essential functions of these intracellular nucleic acids are disrupted. Hybridization is the sequence-specific hydrogen bonding via Watson-Crick base pairs of oligonucleotides to RNA or single-stranded DNA. Such base pairs are said to be complementary to one another.

The naturally occurring events that provide the disruption of the nucleic acid function, discussed by Cohen in *Oligonucleotides: Antisense Inhibitors of Gene Expression*, CRC Press, Inc., Boca Raton, Fla. (1989) are thought to be of two types. The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides (Miller, et al., *Anti-Cancer Drug Design* 1987, 2, 117) and α-anomer oligonucleotides are the two most extensively studied antisense agents which are thought to disrupt nucleic acid function by hybridization arrest.

The second type of terminating event for antisense oligonucleotides involves the enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Considerable research is being directed to the application of oligonucleotides and oligonucleotide analogs as antisense agents for diagnostics, research reagents and potential therapeutic purposes. At least for therapeutic purposes, the antisense oligonucleotides and oligonucleotide analogs must be transported across cell membranes or taken up by cells to express activity. One method for increasing membrane or cellular transport is by the attachment of a pendant lipophilic group.

Ramirez, et al., *J. Am. Chem. Soc.* 1982, 104, 5483, introduced the phospholipid group 5'-O-(1,2-di-O-myristoyl-sn-glycero-3-phosphoryl) into the dimer TpT independently at the 3' and 5' positions. Subsequently Shea, et al., *Nuc. Acids Res.* 1990, 18, 3777, disclosed oligonucleotides having a 1,2-di-O-hexyldecyl-rac-glycerol group linked to a 5'-phosphate on the 5'-terminus of the oligonucleotide. Certain of the Shea, et. al. authors also disclosed these and other compounds in patent application PCT/US90/01002. A further glucosyl phospholipid was disclosed by Guerra, et al., *Tetrahedron Letters* 1987, 28, 3581.

In other work, a cholesteryl group was attached to the inter-nucleotide linkage between the first and second nucleotides (from the 3' terminus) of an oligonucleotide. This work is disclosed in U.S. Pat. No. 4,958,013 and further by Letsinger, et al., *Proc. Natl. Acad. Sci. USA* 1989, 86, 6553. The aromatic intercalating agent anthraquinone was attached to the 2' position of a sugar fragment of an oligonucleotide as reported by Yamana, et al., *Bioconjugate Chem.* 1990, 1, 319. The same researchers placed pyrene-1-methyl at the 2' position of a sugar (Yamana et. al., *Tetrahedron Lett.* 1991, 32, 6347).

Lemairte, et al., *Proc. Natl. Acad. Sci. USA* 1986, 84, 648; and Leonetti, et al., *Bioconjugate Chem.* 1990, 1, 149. The 3' terminus of the oligonucleotides each include a 3'-terminal ribose sugar moiety. The poly(L-lysine) was linked to the oligonucleotide via periodate oxidation of this terminal ribose followed by reduction and coupling through a N-morpholine ring. Oligonucleotide-poly(L-lysine) conjugates are described in European Patent application 87109348.0. In this instance the lysine residue was coupled to a 5' or 3' phosphate of the 5' or 3' terminal nucleotide of the oligonucleotide. A disulfide linkage has also been utilized at the 3' terminus of an oligonucleotide to link a peptide to the oligonucleotide as is described by Corey, et al., *Science* 1987, 238, 1401; Zuckermann, et al., *J. Am. Chem. Soc.* 1988, 110, 1614; and Corey, et al., *J. Am. Chem. Soc.* 1989, 111, 8524.

Nelson, et al., *Nuc. Acids Res.* 1989, 17, 7187 describe a linking reagent for attaching biotin to the 3'-terminus of an oligonucleotide. This reagent, N-Fmoc-O-DMT-3-amino-1,2-propanediol is now commercially available from Clontech Laboratories (Palo Alto, Calif.) under the name 3'-Amine on. It is also commercially available under the name 3'-Amino-Modifier reagent from Glen Research Corporation (Sterling, Va.). This reagent was also utilized to link a peptide to an oligonucleotide as reported by Judy, et al., *Tetrahedron Letters* 1991, 32, 879. A similar commercial reagent (actually a series of such linkers having various lengths of polymethylene connectors) for linking to the 5'-terminus of an oligonucleotide is 5'-Amino-Modifier C6. These reagents are available from Glen Research Corporation (Sterling, Va.). These compounds or similar ones were utilized by Krieg, et al., *Antisense Research and Development* 1991, 1, 161 to link fluorescein to the 5'-terminus of an oligonucleotide. Other compounds of interest have also been linked to the 3'-terminus of an oligonucleotide. Asseline, et al., *Proc. Natl. Acad. Sci. USA* 1984, 81, 3297 described linking acridine on the 3'-terminal phosphate group of an poly (Tp) oligonucleotide via a polymethylene linkage. Haralambidis, et al., *Tetrahedron Letters* 1987, 28, 5199 report building a peptide on a solid state support and then linking an oligonucleotide to that peptide via the 3' hydroxyl group of the 3' terminal nucleotide of the oligonucleotide. Chollet, *Nucleosides & Nucleotides* 1990, 9, 957 attached an Aminolink 2 (Applied Biosystems, Foster City, Calif.) to the 5' terminal phosphate of an oligonucleotide. They then used the bifunctional linking group SMPB (Pierce Chemical Co., Rockford, Ill.) to link an interleukin protein to the oligonucleotide.

An EDTA iron complex has been linked to the 5 position of a pyrimidine nucleoside as reported by Dreyer, et al., *Proc. Natl. Acad. Sci. USA* 1985, 82, 968. Fluorescein has been linked to an oligonucleotide in the same manner as reported by Haralambidis, et al., *Nucleic Acid Research* 1987, 15, 4857 and biotin in the same manner as described in PCT application PCT/US/02198. Fluorescein, biotin and pyrene were also linked in the same manner as reported by Telser, et al., *J . Am. Chem. Soc.* 1989, 111, 6966. A commercial reagent, Amino-Modifier-dT, from Glen Research Corporation (Sterling, Va.) can be utilized to introduce pyrimidine nucleotides bearing similar linking groups into oligonucleotides.

Cholic acid linked to EDTA for use in radioscintigraphic imaging studies was reported by Betebenner, et.al., *Bioconjugate Chem.* 1991, 2, 117; however, it is not known to link cholic acid to nucleosides, nucleotides or oligonucleotides.

OBJECTS OF THE INVENTION

It is one object of this invention to provide nucleosides, oligonucleotides and oligonucleosides that include alkylamino chemical functionality.

It is a further object of the invention to provide compounds having improved transfer across cellular membranes.

It is another object to provide compounds that include intercalators, nucleic acid cleaving agents, cell surface phospholipids, and/or diagnostic agents.

It is yet another object to provide improvements in research and diagnostic methods and materials for assaying bodily states in animals, especially disease states.

It is an additional object of this invention to provide therapeutic and research materials having improved transfer and uptake properties for the treatment of diseases through modulation of the activity of DNA or RNA.

BRIEF DESCRIPTION OF THE INVENTION

These and other objects are satisfied by the present invention, which provides compounds containing alkylamino chemical functionality. In one aspect, the invention provides nucleosides having base portions and ribofuranosyl sugar portions. Such nucleosides bear at a 2'-O-position, a 3'-O-position, or a 5'-O-position a substituent having formula:

—$R_A$—$N(R_{1a})$ ($R_{1b}$)

where:

$R_A$ is alkyl having from 1 to about 10 carbon atoms or $R_A$ is $(CH_2$—$CH_2$—$Q$—$)_x$;

$R_{1a}$, and $R_{1b}$, independently, are H, $R_A$, $R_2$, or an amine protecting group or have formula $C(X)$—$R_2$, $C(X)$—$R_A$—$R_2$, $C(X)$—$Q$—$R_A$—$R_2$, $C(X)$—$Q$—$R_2$;

$R_2$ includes a steroid molecule, a reporter molecule, a lipophilic molecule, a reporter enzyme, a peptide, a protein, or has formula —$Q$—$(CH_2CH_2$—$Q$—$)_x$—$R_3$;

X is O or S;

each Q is, independently, is NH, O, or S;

x is 1 to about 200;

$R_3$ is H, $R_A$, $C(O)OH$, $C(O)OR_A$, $C(O)R_4$, $R_A$—$N_3$, $R_A$—$NH_2$, or $R_A$—$SH$; and $R_4$ is Cl, Br, I, $SO_2R_5$ or has structure:

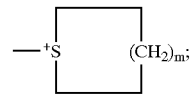

m is 2 to 7; and $R_5$ is alkyl having 1 to about 10 carbon atoms.

In another aspect, the invention provides oligonucleotides and oligonucleosides comprising a plurality of linked nucleosides, wherein each nucleoside includes a ribofuranosyl sugar portion and a base portion and at least one (preferably more than one) of the nucleosides bears at a 2'-O-position, a 3'-O-position, or a 5'-O-position a substituent having formula —$R_A$—$N(R_{1a})$ ($R_{1b}$).

In another aspect the invention provides methods for preparing oligonucleotides and oligonucleosides comprising the steps of contacting nucleosides according to the invention for a time and under reaction conditions effective to form a covalent bond therebetween. In preferred embodiments, at least one of the nucleosides bears a phosphoramidate group at its 2'-O-position or at its 3'-O-position.

In other embodiments, compounds according to the invention are prepared by contacting a nucleoside, oligonucleotide or oligonucleoside with derivatizing reagents. For example, a nucleoside, oligonucleotide or oligonucleoside bearing a 2'-hydroxy group, a 3'-hydroxy group, or a 5'-hydroxy group under basic conditions with a compound having formula $L_1$—$R_A$—$N(R_{1a})$ ($R_{1b}$) wherein $L_1$ is a leaving group such as a halogen and at least one of $R_{1a}$ and $R_{1b}$ is an amine protecting group.

The present invention also provides methods for inhibiting the expression of particular genes in the cells of an organism, comprising administering to said organism a compound according to the invention. Also provided are methods for inhibiting transcription and/or replication of particular genes or for inducing degradation of particular regions of double stranded DNA in cells of an organism by administering to said organism a compound of the invention. Further provided are methods for killing cells or virus by contacting said cells or virus with a compound of the invention. The compound can be included in a composition that further includes an inert carrier for the compound.

DETAILED DESCRIPTION OF THE INVENTION

This invention provides nucleosides, oligonucleotides and oligonucleosides containing alkylamino chemical functionality. The nucleoside subunits can be "natural" or "synthetic" moieties. Each nucleoside is formed from a naturally occurring or synthetic base and a naturally occurring or synthetic pentofuranosyl sugar group.

The term "oligonucleotide" refers to a polynucleotide formed from a plurality of linked nucleotide units. The nucleotides units each include a nucleoside unit. In the context of this invention, the term "oligonucleoside" refers to a plurality of nucleoside units that are linked together. In a generic sense, since each nucleotide unit of an oligonucleotide includes a nucleoside therein, the term "oligonucleoside" can be considered to be inclusive of oligonucleotides (i.e., nucleosides linked together via phosphate linking groups). In a further sense, the term "oligonucleoside" also refers to a plurality of nucleosides that are linked together via linkages other than phosphate linkages. The term "oligonucleoside" thus effectively includes naturally occurring species or synthetic species formed from naturally occurring subunits. For brevity, the term "oligonucleoside" will be used as encompassing both phosphate linked (oligonucleotides) and non-phosphate linked polynucleoside species.

Oligonucleosides according to the invention also can include modified subunits. Representative modifications include modification of a heterocyclic base portion of a nucleoside or a sugar portion of a nucleoside. Exemplary modifications are disclosed in the following U.S. patent applications: Ser. No. 463,358, filed Jan. 11, 1990, entitled Compositions And Methods For Detecting And Modulating RNA Activity; Ser. No. 566,977, filed Aug. 13, 1990, entitled Sugar Modified Oligonucleotides That Detect And Modulate Gene Expression; Ser. No. 558,663, filed Jul. 27, 1990, entitled Novel Polyamine Conjugated oligonucleotides; Ser. No. 558,806, filed Jul. 27, 1991, entitled Nuclease Resistant Pyrimidine Modified Oligonucleotides That Detect And Modulate Gene Expression and Ser. No. PCT/US91/00243, filed Jan. 11, 1991, entitled compositions and Methods For Detecting And Modulating RNA Activity. Each of these patent applications are assigned to the assignee of this invention. The disclosure of each is incorporated herein by reference.

The term oligonucleoside thus refers to structures that include modified portions, be they modified sugar moieties or modified base moieties, that function similarly to natural bases and natural sugars. Representative modified bases include deaza or aza purines and pyrimidines used in place of natural purine and pyrimidine bases; pyrimidines having substituent groups at the 5 or 6 position; and purines having altered or replacement substituent groups at the 2, 6 or 8 positions. Representative modified sugars include carbocyclic or acyclic sugars, sugars having substituent groups at their 2' position, and sugars having substituents in place of one or more hydrogen atoms of the sugar. Other altered base moieties and altered sugar moieties are disclosed in U.S. Pat. No. 3,687,808 and PCT application PCT/US89/02323.

Altered base moieties or altered sugar moieties also include other modifications consistent with the spirit of this invention. Such oligonucleosides are best described as being structurally distinguishable from yet functionally interchangeable with naturally occurring or synthetic wild type oligonucleotides. All such oligonucleosides are comprehended by this invention so long as they function effectively to mimic the structure of a desired RNA or DNA strand.

For use in antisense methodology, the oligonucleosides of the invention preferably comprise from about 10 to about 30 subunits. It is more preferred that such oligonucleosides comprise from about 15 to about 25 subunits. As will be appreciated, a subunit is a base and sugar combination suitably bound to adjacent subunits through, for example, a phosphorous-containing (e.g., phosphodiester) linkage or some other linking moiety. The nucleosides need not be linked in any particular manner, so long as they are covalently bound. Exemplary linkages are those between the 3'- and 5'-positions or 2'- and 5'-positions of adjacent nucleosides. Exemplary linking moieties are disclosed in the following references: Beaucage, et al., *Tetrahedron* 1992, 48, 2223 and references cited therein; and U.S. patent applications: Ser. No. 703,619, filed May 21, 1991; Ser. No. 903,160, filed Jun. 24, 1992; Ser. No. 039,979, filed Mar. 20, 1993; Ser. No. 039,846, filed Mar. 30, 1993; and Ser. No. 040,933, filed Mar. 31, 1993. Each of the foregoing patent applications are assigned to the assignee of this invention. The disclosure of each is incorporated herein by reference.

It is preferred that the RNA or DNA portion which is to be modulated using oligonucleosides of the invention be preselected to comprise that portion of DNA or RNA which codes for the protein whose formation or activity is to be modulated. The targeting portion of the composition to be employed is, thus, selected to be complementary to the preselected portion of DNA or RNA, that is, to be an antisense oligonucleoside for that portion.

In accordance with one preferred embodiment of this invention, the compounds of the invention hybridize to HIV mRNA encoding the tat protein, or to the TAR region of HIV mRNA. In another preferred embodiment, the compounds mimic the secondary structure of the TAR region of HIV mRNA, and by doing so bind the tat protein. Other preferred compounds are complementary to sequences for herpes, papilloma and other viruses.

The nucleosides and oligonucleosides of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, since each cell of multicellular eukaryotes can be treated since they include both DNA-RNA transcription and RNA-protein translation as integral parts of their cellular activity. Many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides. As used herein, therapeutics is meant to include the eradication of a disease state, by killing an organism or by control of erratic or harmful cellular growth or expression.

In one aspect, the present invention is directed to nucleosides and oligonucleosides that bear at least one amine-containing substituent at a position. Such substituents preferably have formula —$R_A$—$N(R_{1a})(R_{1b})$ and are appended at 2'-O-, 3'-O-, and/or 5'-O-positions.

Each $R_A$ according to the invention is an alkyl moiety independently selected to having 1 to about 10 carbon atoms or $R_A$ is a polyether, a polythioether or polyalkylamine. The term "alkyl" is intended to include straight chain and branched hydrocarbons. The preferred length of these hydrocarbons is 1 to about 7 carbon atoms.

$R_{1a}$ and $R_{1b}$ according to the invention are H, $R_A$, $R_2$, an amine protecting group, or have formula C(X)—$R_2$, C(X)—$R_A$—$R_2$, C(X)—Q—$R_A$—$R_2$, C(X)—Q—$R_2$. Protecting groups are known per se as chemical functional groups that can be selectively appended to and removed from functionalities, such as amine groups. These groups are present in a chemical compound to render such functionality inert to chemical reaction conditions to which the compound is exposed. See, e.g., Greene and Wuts, Protective Groups in Organic Synthesis, 2d edition, John Wiley & Sons, New York, 1991. Numerous amine protecting groups are known in the art, including, but not limited to: phthalimide (PHTH), trifluoroacetate (triflate), allyloxycarbonyl (Alloc), benzyloxycarbonyl (CBZ), chlorobenzyloxycarbonyl, t-butyloxycarbonyl (Boc), fluorenylmethoxycarbonyl (Fmoc), and isonicotinyloxycarbonyl (i-Noc) groups. (see, e.g., Veber and Hirschmann, et al., *J. Org. Chem.* 1977, 42, 3286 and Atherton, et al., The Peptides, Gross and Meienhofer, Eds, Academic Press; New York, 1983; Vol. 9 pp. 1–38).

$R_2$ can include a steroid molecule, a reporter molecule, a lipophilic molecule, a reporter enzyme, a peptide, a protein (i.e., a substituent consisting essentially of same), or a molecule having formula —Q—(CH$_2$CH$_2$—Q—)$_x$—R$_3$. For the purposes of this invention the terms "reporter molecule" and "reporter enzyme" are inclusive of those molecules or enzymes that have physical or chemical properties that allow them to be identified in gels, fluids, whole cellular systems, broken cellular systems and the like utilizing physical properties such as spectroscopy, radioactivity, colorimetric assays, fluorescence, and specific binding. Steroids include those chemical compounds that contain a perhydro-1,2-cyclopentanophenanthrene ring system. Proteins and peptides are utilized in their usual sense as polymers of amino acids. Normally peptides comprise such polymers that contain a smaller number of amino acids per unit molecule than do the proteins. Lipophilic molecules include naturally-occurring and synthetic aromatic and non-aromatic moieties such as fatty acids, esters, alcohols and other lipid molecules, substituted aromatic groups such as dinitrophenyl groups, cage structures such as adamantane and buckninsterfullerenes, and aromatic hydrocarbons such as benzene, perylene, phenanthrene, anthracene, naphthalene, pyrene, chrysene, and naphthacene.

Particularly useful as steroid molecules are the bile acids including cholic acid, deoxycholic acid and dehydrocholic acid; steroids including cortisone, digoxigenin, testosterone and cholesterol and even cationic steroids such as cortisone having a trimethylaminomethyl hydrazide group attached via a double bond at the 3 position of the cortisone rings. Particularly useful as reporter molecules are biotin, dinitrophenyl, and fluorescein dyes. Particularly useful as lipophilic molecules are alicyclic hydrocarbons, saturated and unsaturated fatty acids, waxes, terpenes and polyalicyclic hydrocarbons including adamantane and buckminsterfullerenes. Particularly useful as reporter enzymes are alkaline phosphatase and horseradish peroxidase. Particularly useful as peptides and proteins are sequence-specific peptides and proteins including phosphodiesterase, peroxidase, phosphatase and nuclease proteins. Such peptides and proteins include SV40 peptide, RNaseA, RNase H and Staphylococcal nuclease. Particularly useful as terpenoids are vitamin A, retinoic acid, retinal and dehydroretinol.

$R_2$ also can have formula —Q—(CH$_2$CH$_2$—Q—)$_x$—R$_3$, where Q is O, S, or NH. Subscript x can be 1 to about 200, preferably about 20 to about 150, more preferably about 10 to about 50. Preferably, Q are selected to be O, such that $R_2$ constitutes a poly(ethyleneglycol) (PEG) group (i.e., $R_3$=H) or a functionalized derivative thereof (e.g., $R_3$=C(O)Cl). $R_3$ can be H, $R_A$, C(O)OH, C(O)OR$_A$, C(O)R$_4$, $R_A$—N$_3$, $R_A$—NH$_2$ or $R_A$—SH where $R_4$ is F, Cl, Br, I, SO$_2$R$_5$ or a small thio-containing heterocycle having structure:

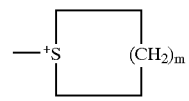

where m is 2 to 7. Representative PEG-containing $R_2$ groups are disclosed by Ouchi, et al., *Drug Design and Discovery* 1992, 9, 93, Ravasio, et al., *J. Org. Chem.* 1991, 56, 4329, and Delgardo et. al., Critical Reviews in Therapeutic Drug Carrier Systems 1992, 9, 249.

Oligonucleosides according to the invention can be assembled in solution or through solid-phase reactions, for example, on a suitable DNA synthesizer utilizing nucleosides according to the invention and/or standard nucleotide precursors. The nucleosides and nucleotide precursors can already bear alkylamino groups or can be later modified to bear such groups.

In the former case, compounds according to the invention are prepared by, for example, reacting nucleosides bearing at least one free 2'-, 3'-, or 5'-hydroxyl group under basic conditions with a compound having formula $L_1$—(CH$_2$)$_n$—N($R_{1a}$) ($R_{1b}$) where $L_1$ is a leaving group and at least one of $R_{1a}$ and $R_{1b}$ is an amine protecting group. Displacement of the leaving group through nucleophilic attack of an oxygen anion produces the desired amine derivative. Leaving groups according to the invention include but are not limited to halogen, alkyl-sulfonyl, substituted alkylsulfonyl, arylsulfonyl, substituted arylsulfonyl, hetercyclcosulfonyl or trichloroacetimidate. A more preferred group includes chloro, fluoro, bromo, iodo, p-(2,4-dinitroanilino) benzenesulfonyl, benzenesulfonyl, methyl-sulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl, with bromo being preferred.

Suitably protected nucleosides can be assembled into an oligonucleosides according to known techniques. See, e.g., Beaucage, et al., *Tetrahedron* 1992, 48, 2223.

Oligonucleosides according to the invention also can be prepared by assembling an oligonucleoside and appending alkylamino functionality thereto. For example, oligonucleosides having free hydroxyl groups can be assembled according to known techniques and then reacted with a reagent having formula $L_1$-(CH$_2$)$_n$—N($R_{1a}$) ($R_{1b}$). As will be recognized, however, greater selectivity can be achieved in terms of placement of alkylamino functionality within an oligonucleoside by introducing such functionality, as discussed above, on selected nucleosides and then using both the selected nucleosides and other nucleosides to construct an oligonucleoside.

Once assembled, an oligonucleoside bearing one or more groups having formula —$R_A$—N($R_{1a}$) ($R_{1b}$) wherein at least one of $R_{1a}$ and $R_{1b}$ is a protecting group is treated with reagents effective to remove the protecting group. Once deprotected, the oligonucleoside can be contacted with electrophillic moieties such as, for example, succinimidyl esters and other activated carboxylic acids including C(=O)—O-succinimide and C(=O)—O-pentafluorophenyl, isothiocyanates, sulfonyl chlorides, halacetamides, phospholipid carbocyclic acid active esters, o-phenanthroline-5-iodoacetamide, fluorescein isothiocyanate, 1-pyrene butyric acid-N-hydroxy succinimide ester and carboxylic acid derivatives of PNA (carboxylic acid derivatives of peptide nucleic acids). Preferred electrophillic moieties include cholesteryl-3-hemisuccinate-N-hydroxy succinimide ester, pyrene-1-butyric acid-N-hydroxy succinimide ester and polyethylene glycol-propionic acid-N-hydroxy succimide ester.

Thus, the invention first builds the desired linked nucleoside sequence in the normal manner on the DNA synthesizer. One or more (preferably two or more) of the linked nucleosides are then functionalized or derivatized with the lipophilic steroid, reporter molecule, lipophilic molecule, reporter enzyme, peptide or protein.

Additional objects, advantages, and novel features of this invention will become apparent to those skilled in the art upon examination of the following examples, which are not intended to be limiting. All oligonucleotide sequences are listed in a standard 5' to 3' order from left to right.

EXAMPLE 1

Oligonucleotides Having 2'-Protected-Amine Terminating Linking Group

A. Preparation of 5'-Dimethoxytrityl-2'-(O-Pentyl-N-phthalimido)-2'-Deozyadenosine Phosphoramidite.

To introduce a functionalization at the 2' position of nucleotides within desired oligonucleotide sequences, 5'-dimethoxytrityl-2'-(O-pentyl-N-phthalimido)-2'-deoxyadenosine phosphoramidite was utilized to provide a linking group attached to the 2' position of nucleotide components of an oligonucleotide. This compound was synthesized generally in accordance with the procedures of patent application Ser. Nos. US91/00243 and 463,358, identified above, starting from adenosine. Briefly, this procedure treats adenosine with NaH in dimethylformamide (DMF) followed by treatment with N-(5-bromopentyl)phthalimide. Further treatment with $(CH_3)_3SiCl$, Ph—C(O)—Cl and $NH_4OH$ yields N6-benzyl protected 2'-pentyl-N-phthalimido functionalized adenosine. Treatment with DIPA and $CH_2Cl_2$ adds a DMT blocking group at the 5' position. Finally phosphitylation gives the desired phosphoramidite compound. This compound was utilized in the DNA synthesizer as a 0.09M solution in anhydrous $CH_3CN$. Oligonucleotide synthesis was carried out in either an ABI 390B or an ABI 394 synthesizer employing the standard synthesis cycles with an extended coupling time of 10 minutes during coupling of Compound 2 into the oligonucleotide sequence. Coupling efficiency of greater than 98% was observed.

B. 2'-Pr tect d-Amin Linking Group Containing Phosphodiester Oligonucleotid s

The following oligonucleotides having phosphodiester inter-nucleotide linkages were synthesized:

Oligomer 9: 5' TA*G 3';

Oligomer 10: 5' CCA*G 3';

Oligomer 11 (SEQ ID NO:1): 5' GGC TGA* CTG CG 3';

Oligomer 12 (SEQ ID NO:2): CTG TCT CCA* TCC TCT TCA CT;

Oligomer 13: CTG TCT CCA* TCC TCT TCA* CT wherein A* represents a nucleotide functionalized to incorporate a pentyl-N-phthalimido functionality. Oligomers 12 and 13 are antisense compounds to the E2 region of the bovine papilloma virus-1 (BPV-1). Oligomers 12 and 13 have the same sequence as Oligomer 3 in application Ser. No. 782,374, except for the 2' modification. The oligonucleotides were synthesized in either a 10 μmol scale or a 3×1 μmol scale in the "Trityl-On" mode. Standard deprotection conditions (30% $NH_4OH$, 55° C., 24 hours) were employed. The oligonucleotides were purified by reverse phase HPLC (Waters Delta-Pak $C_4$ 15 μm, 300A, 25×100 mm column equipped with a guard column of the same material). They were detritylated and further purified by size exclusion using a Sephadex G-25 column. NMR analyses by both proton and phosphorus NMR confirmed the expected structure for the Oligomers 9 and 10.

C. 2'-Protected-Amine Linking Group Containing Phosphorothioate Oligonucleotides The following oligonucleotides having phosphorothioate inter-nucleotide linkages were synthesized:

Oligomer 14 (SEQ ID NO:3): $T_sT_sG_s$ $C_sT_sT_s$ $_{Cs}C_sA^*_s$ $T_sC_sT_s$ $T_sC_sC_s$ $T_sC_sG_s$ $T_sC$;

Oligomer 15 (SEQ ID NO:4): $T_sG_sG_s$ $G_sA_sG_s$ $C_sC_sA_s$ $T_sA_sG_s$ $C_sG_sA^*_s$ $G_sG_sC$; and Oligomer 16: $T_sG_sG_s$ $G_sA^*_sG_s$ $C_sC_sA^*_s$ $T_sA^*_sG_s$ $C_sG_sA^*_s$ $G_sG_sC$ wherein A* represents a nucleotide functionalized to incorporate a pentyl-N-phthalimido functionality and the subscript "s" represents a phosphorothioate inter-nucleotide backbone linkage. Oligomer 14 is an antisense compound directed to the E2 region of the bovine papilloma virus-1 (BPV-1). Oligomers 15 and 16 are antisense compounds to ICAM. Oligomer 14 has the same sequence as Oligomer 3 in application Ser. No. 782,374, except for the 2' modification whereas Oligomers 15 and 16 have the same sequence as Oligomer 4 in application Ser. No. 782,374 except for the 2' modification. These oligonucleotides were synthesized as per the method of Example 1(B) except during the synthesis, for oxidation of the phosphite moieties, the Beaucage reagent (i.e., 3H-1,2-benzodithioate-3-one 1,1-dioxide, see, Radhakrishnan, et al., J. Am. Chem. Soc. 1990, 112, 1253) was used as a 0.24 M solution in anhydrous $CH_3CN$ solvent. The oligonucleotides were synthesized in the "Trityl-On" mode and purified by reverse phase HPLC utilizing the purification procedure of Example 1(B).

D. 2'-O-Methyl Derivatized, 2'-Protected-Amine Linking Group containing RNA Oligonucleotides The following oligonucleotides having 2'-O-methyl groups on each nucleotide not functionalized with a 2'-protected amine functionalization were synthesized:

Oligomer 17: CCA A*GC CUC AGA; and

Oligomer 18: CCA GGC UCA GA*T wherein A* represents a nucleotide functionalized to incorporate a pentyl-N-phthalimido functionality and where the remaining nucleotides except the 3'-terminus nucleotide are each 2'-O-methyl derivatized nucleotides. The 3'-terminus nucleotide in both oligomers 17 and 18 is a 2'-deoxy nucleotide. Both Oligomers 17 and 18 are antisense compounds to the HIV-1 TAR region. The oligonucleotides were synthesized as per the method of Example 6 in application Ser. No. 782,374 (utilizing Compound 2 thereof) for introduction of the nucleotides containing the pentyl-N-phthalimido functionality and appropriate 2-O-methyl phosphoramidite nucleotides from Chemgenes Inc. (Needham, Mass.) for the remaining RNA nucleotides. The 3'-terminus terminal 2'-deoxy nucleotides were standard phosphoamidites utilized for the DNA synthesizer. The oligonucleotides were deprotected and purified as per the method of Example 1(B).

EXAMPLE 2

Functionalization of Oligonucleotides At the 2' Position

A. Functionalisation with Biotin

1. Single Site Modification

About 10 O.D. units ($A_{260}$) of Oligomer 12 (see, Example 1) (approximately 60 nmols based on the calculated extinction coefficient of $1.6756\times10^5$) was dried in a microfuge tube. The oligonucleotide was dissolved in 200 μl of 0.2 M NaHCO$_3$ buffer and D-biotin-N-hydroxysuccinimide ester (2.5 mg, 7.3 μmols) (Sigma, St. Louis, Mo.) was added followed by 40 μl DMF. The solution was let stand overnight. The solution was applied to a Sephadex G-25 column (0.7×15 cm) and the oligonucleotide fractions were combined. Analytical HPLC showed nearly 85% conversion to the product. The product was purified by HPLC (Waters 600E with 991 detector, Hamilton PRP-1 column 0.7×15 cm; solvent A: 50 mM TEAA pH 7.0; B: 45 mM TEAA with 80% acetonitrile: 1.5 ml flow rate: Gradient: 5% B for first 5 minutes, linear (1%) increase in B every minute thereafter) and further desalted on Sephadex G-25 to give the oligonucleotide:

Oligomer 19 (SEQ ID NO:5): CTG TCT CCA* TCC TCT TCA CT wherein A represents a nucleotide functionalized to incorporate a biotin functionality linked via a 2'-O-pentyl-amino linking group to the 2' position of the designated nucleotide. HPLC retention times are shown in Table 1 below.

2. Multiple Site Modification

About 10 O.D. units (A$_{260}$) of Oligomer 13 (see, Example 1, approximately 60 nmols) was treated utilizing the method of Example B(A)(1) in application Ser. No. 782,374 with D-biotin-N-hydroxysuccinimide ester (5 mg) in 300 μl of 0.2 M NaHCO$_3$ buffer/50 μl DMF. Analytical HPLC showed 65% of double labeled oligonucleotide product and 30% of single labeled products (from the two available reactive sites). HPLC and Sephadex G-25 purification gave the oligonucleotide:

Oligomer 20: CTG TCT CCA* TCC TCT TCA*CT wherein A* represents nucleotides functionalized to incorporate a biotin functionality linked via a 2'-O-pentyl-amino linking group to the 2' position of the designated nucleotide. HPLC retention times for this product (and its accompanying singly labeled products) are shown in Table 1 below.

B. Functionalization with Fluorescein

1. Single Site Modification

A 1M Na$_2$CO$_3$/1M NaHCO$_3$ buffer (pH 9.0) was prepared by adding 1M NaHCO$_3$ to 1M Na$_2$CO$_3$. A 200 μl portion of this buffer was added to 10 O.D. units of Oligomer 12 (see, Example 1) in a microfuge tube. A 10 mg portion of fluorescein-isocyanate in 500 μl DMF was added to give a 0.05 M solution. A 100 μl portion of the fluorescein solution was added to the oligonucleotide solution in the microfuge tube. The tube was covered with aluminum foil and let stand overnight. The reaction mixture was applied to a Sephadex G-25 column (0.7×20 cm) that had been equilibrated with 25% (v/v) ethyl alcohol in water. The column was eluted with the same solvent. Product migration could be seen as a yellow band well separated from dark yellow band of the excess fluorescein reagent. The fractions showing absorption at 260 nm and 485 nm were combined and purified by HPLC as per the purification procedure of Example 2(A)(1). Analytical HPLC indicated 81% of the desired doubly functionalized oligonucleotide. The product was lyophilized and desalted on Sephadex to give the oligonucleotide:

Oligomer 21Q ID NO:9): CTG TCT CCA* TCC TCT TCA CT wherein A* represents a nucleotide functionalized to incorporate a fluorescein functionality linked via a 2'-O-pentyl-amino linking group to the 2' position of the designated nucleotide. HPLC retention times are shown in Table 1 below.

2. Multiple site Modification

A 10 O.D. unit (A$_{260}$) portion of Oligomer 13 (from Example 1) was dissolved in 300 μl of the 1M Na$_2$HCO$_3$/1M Na$_2$CO$_2$ buffer of Example 2(B)(1) and 200 μl of the fluorescein-isothiocyanate stock solution of Example 2(B)(1) was added. The resulting solution was treated as per Example 2(B)(1). Analytical HPLC indicated 61% of doubly labeled product and 38% of singly labeled products. Work up of the reaction gave the oligonucleotide:

Oligomer 22: CTG TCT CCA* TCC TCT TCA* CT wherein A* represents nucleotides functionalized to incorporate a fluorescein functionality linked via a 2'-O-pentyl-amino linking group to the 2' position of the designated nucleotide. HPLC retention times are shown in Table 1 below.

C. Functionalization with Cholic Acid

1. Single Site Modification

A 10 O.D. unit (A$_{260}$) portion of Oligomer 12 (see, Example 1) was treated with cholic acid-NHS ester (Compound 1 in application Ser. No. 782,374, 5 mg, 9.9 μmols) in 200 μl of 0.2 M NaHCO$_3$ buffer/40 μl DMF. The reaction mixture was heated for 16 hours at 45° C. The product was isolated as per the method of Example 2(B)(1). Analytical HPLC indicated greater than 85% product formation. Work up of the reaction gave the oligonucleotide:

Oligomer 23: CTG TCT CCA* TCC TCT TCA CT wherein A* represents a nucleotide functionalized to incorporate a cholic acid functionality linked via a 2'-O-pentyl-amino linking group to the 2' position of the designated nucleotide. HPLC retention times are shown in Table 1 below.

2. Multiple Site Modification

A 10 O.D. unit (A$_{260}$) portion of Oligomer 13 (see, Example 1) was treated with cholic acid-NHS ester (Compound 1 in application Ser. No. 782,374, 10 mg, 19.8 μmols) in 300 μl of 0.2 M NaHCO$_3$ buffer/50 μl DMF. The reaction mixture was heated for 16 hours at 45° C. The product was isolated as per the method of Example 2(A)(1). Analytical HPLC revealed 58% doubly labeled product, 17% of a first singly labeled product and 24% of a second singly labeled product. Work up as per Example 2(A)(1) gave the oligonucleotide:

Oligomer 24: CTG TCT CCA* TCC TCT TCA* CT wherein A* represents nucleotides functionalized to incorporate a cholic acid functionality linked via a 2'-O-pentyl-amino linking group to the 2' position of the designated nucleotide. HPLC retention times are shown in Table 1 below.

D. Functionalization with Digoxigenin

1. Single Site Modification

A 10 O.D. unit (A$_{260}$) portion of Oligomer 12 (see, Example 1) was treated with digoxigenin-3-O-methylcarbonyl-ε-aminocaproic N-hydroxy succinimide ester (Boehringer Mannheim Corporation, Indianapolis, Ind.) in 200 μl of 0.1 M borate pH 8.3 buffer/40 μl DMF. The reaction mixture was let stand overnight. The product was isolated as per the method of Example 2(A)(1). Work up of the reaction gave the oligonucleotide:

Oligomer 25: CTG TCT CCA* TCC TCT TCA CT wherein A* represents a nucleotide functionalized to incorporate a digoxigenin functionality linked via a 2'-O-pentyl-amino linking group to the 2' position of the designated nucleotide. HPLC retention times are shown in Table 1 below.

2. Multiple site Modification

A 10 O.D. units (A$_{260}$) portion of Oligomer 13 (see, Example 1) was treated with digoxigenin-3-O-methylcarbonyl-ε-aminocaproic N-hydroxy succinimide ester (Boehringer Mannheim Corporation, Indianapolis, Ind.) in 300 μl of 0.1 M borate pH 8.3 buffer/50 μl DMF. The reaction mixture was let stand overnight. The product was isolated as per the method of Example 2(A)(1). Work up as per Example 2(A)(1) gave the oligonucleotide:

Oligomer 26: CTG TCT CCA* TCC TCT TCA* CT wherein A* represents nucleotides functionalized to incorporate a cholic acid functionality linked via a 2'-O-pentyl-amino linking group to the 2' position of the designated nucleotide. HPLC retention times are shown in Table 1 below.

TABLE 1

HPLC Retention Times of Oligonucleotides Functionaliz d At 2' Position

| Oligomer | Retention Time Minutes | |
|---|---|---|
| | Mono Substitution | Multiple Substitution |
| Oligomer 12[1] | 21.78 | |
| Oligomer 13[1] | | 22.50 |
| Oligomer 19[2] | 23.58 | |
| Oligomer 20[2] | | 24.16[a]   25.19[b] |
| Oligomer 21[3] | 26.65 | |
| Oligomer 22[3] | | 26.99[a]   29.33[b] |
| | | 27.55[a] |
| Oligomer 23[4] | 30.10 | |
| Oligomer 24[4] | | 30.38[a]   37.00[b] |
| | | 32.22[a] |
| Oligomer 25[5] | 28.06 | |
| Oligomer 26[5] | | 28.14[a]   33.32[b] |
| | | 29.24[a] |

Conditions: Waters 600E with 991 detector, Hamilton PRP-1 column 0.7 × 15 cm; solvent A: 50 mM TEAA pH 7.0; B: 45 mM TEAA with 80% acetonitrile: 1.5 ml flow rate: Gradient: 5% B for first 5 minutes, linear (1%) increase in B every minute thereafter;
[a]Mono conjugated minor product;
[b]Doubly conjugated major product;
[1]Parent Oligonucleotide - no 2' functionalization;
[2]2' Biotin functionalization;
[3]2' Fluorescein functionalization;
[4]2' Cholic Acid functionalization; and
[5]2' Digoxigenin functionalization.

Procedure A

Confirmation of Structure of Functionalized Oligonucleotides Containing A Tethered 2'-Amino Moiety Oligonucleotides of the invention were digested with snake venom phosphodiesterase and calf-intestine alkaline phosphatase to their individual nucleosides. After digestion, the nucleoside composition was analyzed by HPLC. The HPLC analysis established that functionalized nucleotide compounds having the tethered 2'-amino moiety thereon were correctly incorporated into the oligonucleotide.

Snake venom phosphodiesterase [Boehringer-Mannheim cat. #108260, 1 mg (1.5 units)/0.5 ml] and alkaline phosphatase from calf intestine (1 unit/microliter, Boehringer-Mannheim cat. # 713023) in Tris-HCl buffer (pH 7.2, 50 mM) were used to digest the oligonucleotides to their component nucleosides. To 0.5 O.D. units of oligonucleotide in 50 μl buffer (nearly 40 μM final concentration for a 20 mer) was added 5 μl of snake venom phosphodiesterase (nearly 0.3 units/mL, final concentration) and 10 μl of alkaline phosphatase (app. 150 units/mL, final concentration). The reaction mixture was incubated at 37° C. for 3 hours. Following incubation, the reaction mixture was analyzed by HPLC using a reverse phase analytical column (app. 30×2.5 cm); solvent A: 50 mM TEAA pH 7; solvent B: acetonitrile; gradient 100% for 10 minutes, then 5% B for 15 minutes, then 10% B and then wash. The results of these digestion are shown in Table 2 for representative oligonucleotides.

TABLE 2

OLIGONUCLEOTIDE ANALYSIS VIA ENZYMATIC DIGESTION

| | | Observed Ratios** | | | | |
|---|---|---|---|---|---|---|
| Oligomer | Abs. max. | 267 C | 252 G | 267 T | 260 A* | A |
| Oligomer 10 | 2 | 1 | | 1 | | |
| Oligomer 11 | 3 | 5 | 2 | 1 | | |
| Oligomer 12 | 9 | 1 | 8 | 1 | 1 | |
| Oligomer 13 | 9 | 1 | 8 | 2 | | |

*Nucleoside having 2'-O-linker attached thereto; and
**Corrected to whole numbers.

As is evident from Table 2, the correct nucleoside ratios are observed for the component nucleotides of the test oligonucleotides.

Procedure B

Determination of Melting Temperatures (Tm's) of Cholic Acid Oligonucleotide Conjugates The relative ability of oligonucleotides to bind to their complementary strand is compared by determining the melting temperature of the hybridization complex of the oligonucleotide and its complementary strand. The melting temperature (Tm), a characteristic physical property of double helices, denotes the temperature in degrees centigrade at which 50% helical versus coil (un-hybridized) forms are present. Tm is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$. The higher the Tm, the greater the strength of the binding of the strands. Non-Watson-Crick base pairing has a strong destabilizing effect on the Tm. Consequently, absolute fidelity of base pairing is necessary to have optimal binding of an antisense oligonucleotide to its targeted RNA.

1. Terminal End Conjugates a. Synthesis

A series of oligonucleotides were synthesized utilizing standard synthetic procedures (for un-functionalized oligonucleotides) or the procedure of Example 3(A) in application Ser. No. 782,374 for oligonucleotides having a 5'-terminus amino linker bearing oligonucleotide or the procedure of Example 3(B) in application Ser. No. 782,374 for 5'-terminus cholic acid-bearing oligonucleotides. Each of the oligonucleotides had the following 5-LO antisense sequence: 5' TCC AGG TGT CCC CAT C 3' (SEQ ID NO:6). The nucleotides were synthesized on a 1.0 μmol scale. Oligomer 32 was the parent compound having normal phosphodiester inter-nucleotide linkages. Oligomer 33 incorporated phosphorothioate inter-nucleotide linkages in the basic oligonucleotide sequence. Oligomer 34 is a an intermediate oligonucleotide having a 5'-aminolink at the 5'-terminus of the basic oligonucleotide sequence and Oligomer 35 was a similar 5'-aminolink compound incorporating phosphorothioate inter-nucleotide linkages. Oligomer 36 is a 5'-terminus cholic acid conjugate of the basic phosphodiester oligonucleotide sequence while Oligomer 37 is a similar 5'-cholic acid conjugate incorporating phosphorothioate inter-nucleotide linkages. Oligomers 32 and 33 were synthesized in a "Trityl-On" mode and were purified by HPLC. Oligomers 34 and 35 were synthesized as per Example 30(A) in application Ser. No. 782,374 without or with Beaucage reagent treatment, to yield phosphodiester or phosphorothioate inter-nucleotide linkages, respectively. Oligomers 36 and 37 were prepared from samples of Oligomers 34 and 35, respectively, utilizing a solution of cholic acid N-hydroxysuccinimide ester (Compound 1) 1 dissolved in DMF as per Example 3(B) in application Ser. No. 782,374. Oligomers 36 and 37 were purified by HPLC. The products were concentrated and desalted in a Sephadex G-25 column. Gel electrophoresis analyses also confirmed a pure product with the pure conjugate moving slower than the parent oligonucleotide or 5'-amino functionalized oligonucleotide.

b. Melting Analysis

The test oligonucleotides [either the phosphodiester, phosphorothioate, cholic acid conjugated phosphodiester, cholic acid conjugated phosphorothioate or 5'-aminolink intermediate phosphodiester or phosphorothioate oligonucleotides of the invention or otherwise] and either the complementary DNA or RNA oligonucleotides were incubated at a standard concentration of 4 μM for each oligonucleotide in buffer (100 mM NaCl, 10 mM Na-phosphate, pH 7.0, 0.1 mM EDTA). Samples were heated to 90 degrees C. and the initial absorbance taken using a Guilford Response II spectrophotometer (Corning). Samples were then slowly cooled to 15 degrees C. and then the change in absorbance at 260 nm was monitored during the heat denaturation procedure. The temperature was elevated 1 degree/ absorbance reading and the denaturation profile analyzed by taking the 1st derivative of the melting curve. Data was also analyzed using a two-state linear regression analysis to determine the Tm's. The results of these tests are shown in Table 3 as are the HPLC retention times of certain of the test compounds.

TABLE 3

Melting Temperature of The Hybridization Complex Of The Oligonucleotide And Its Complimentary Strand

| Oligomer | Tm** DNA | Tm** RNA | HPLC Ret. Time* minutes |
|---|---|---|---|
| 32 | 62.6 | 62.0 | — |
| 33 | 55.4 | 54.9 | — |
| 34 | ND | ND | 13.6 |
| 35 | ND | ND | 17.0 |
| 36 | 63.4 | 62.4 | 22.0 |
| 37 | 56.3 | 55.8 | 22.5 |

*HPLC conditions: Walters Delta Pak C-18 RP 2.5u column; at 0 min 100% 0.1 TEAA; at 30 min 50% TEAA and 50% Acetonitrile: Flow rate 1.0 ml/min.
**Tm at 4 μM each strand from fit of duplicate melting curves to 2-state model with linear sloping base line. Conditions: 100 mM NaCl, 10 mM Phosphate, 0.1 mM EDTA, pH 7.0.
ND = not determined As is evident from Table 2, conjugates of cholic acid at the end of the oligonucleotide do not affect the Tm of the oligonucleotides.

2. Strands Incorporating 2'-O-Pentylamino Linker a. Synthesis

An oligonucleotide of the sequence:

Oligomer 38 (SEQ ID NO:7): GGA* CCG GA*A* GGT A*CG A*G wherein A* represents a nucleotide functionalized to incorporate a pentylamino functionality at its 2'-position was synthesized in a one micromole scale utilizing the method of Example 1(B). The oligonucleotide was purified by reverse phase HPLC, detritylated and desalted on Sephadex G-25. PAGE gel analysis showed a single band. A further oligonucleotide, Oligomer 39, having the same sequence but without any 2'-O-amino linker was synthesis in a standard manner. A complementary DNA oligonucleotide of the sequence:

Oligomer 40 (SEQ ID NO:8): CCT GGC CTT CCA TGC TC was also synthesized in a standard manner as was a complementary RNA oligonucleotide of the sequence:

Oligomer 41 (SEQ ID NO:9): CCU GGC CUU CCA UGC UC.

b. Melting Analysis

Melting analysis was conducted as per the method of Procedure B(1)(b). The results are shown in Table 4.

TABLE 4

Melting Temperature Of The Hybridization Complex Of The Oligonucleotide And Its Complementary Strand

| Oligomer | Tm* DNA[1] | Tm* RNA[2] |
|---|---|---|
| 38 | 54.5 | 58.0 |
| 39 | 60.6 | 56.9 |

*Tm at 4 μM each strand from fit of duplicate melting curves to 2-state model with linear sloping base line. Conditions: 100 mM NaCl, 10 mM Phosphate, 0.1 mM EDTA, ph 7.0.
[1]Against DNA complementary strand, Oligomer 40.
[2]Against RNA complementary strand, Oligomer 41

As is evident from Table 4 against the RNA complementary strand the change in Tm's between the strand having 2'-amino linkers thereon and the unmodified strand is 1.1 degrees (0.22 change per modification). Against the DNA strand, the change is −6.1 degrees (−1.2 change per modification). When compared to the parent unmodified oligonucleotide the 2'-amino linker-containing strand has a stabilizing effect upon hybridization with RNA and a destabilizing effect upon hybridization with DNA.

Compounds of the invention were tested for their ability to increase cellular uptake. This was d termined by judging either their ability to inhibit the expression of bovine papilloma virus-1 (BPV-1) or an assay involving luciferase production (for HIV-1).

Procedure C

Determination of Cellular Uptake Judged By The Inhibition Of Expression of Bovine Papilloma Virus-1 (bpv-1) As Measured By an E2 Transactivation Assay For this test, a phosphorothioate oligonucleotide analog of the sequence:

Oligomer 42: CTG TCT CCA TCC TCT TCA CT was used as the basic sequence. This sequence is designed to be complementary to the translation initiation region of the E2 gene of bovine papilloma virus type 1 (BPV-1). Oligomer 42 served as the positive control and standard for the assay. Oligomer 3 (from Example 4 in application Ser. No. 782,374) served as a second test compound. It has the same basic sequence except it is a phosphorothioate oligonucleotide and further it has a cholic acid moiety conjugated at the 3'-end of the oligonucleotide. Oligomer 2 (from Example 2 in application Ser. No. 782,374) served as a third test compound. Again it is of the same sequence, it is a phosphorothioate oligonucleotide and it has a cholic acid moiety conjugated at the 5'-end. Oligomer 5 (from Example 5 in application Ser. No. 782,374) served as a fourth test compound. Once again it has the same sequence, is a phosphorothioate oligonucleotide and it has a cholic acid moiety conjugated at both the 3'-end and 5'-end. A fifth test compound was a phosphorothioate oligonucleotide with no significant sequence homology with BPV-1. A sixth test compound was a further phosphorothioate oligonucleotide with no significant sequence homology with BPV-1. The last test compound, the seventh test compound, was a phosphorothioate oligonucleotide with cholic acid conjugated to the 3'-end but having no significant sequence homology with BPV-1. Compounds five, six and seven served as negative controls for the assay.

For each test I-38 cells were plated at 5×10$^4$ cells per cm2 in 60 mm petri dishes. Eight hours after plating, medium was aspirated and replaced with medium containing the test oligonucleotide and incubated overnight. Following incubation, medium was aspirated and replaced with fresh medium without oligonucleotide and incubated for one hour. Cells were then transfected by the CaPO$_4$ method with 2 µg of pE2RE-1-CAT. After a four hour incubation period cells were glycerol shocked (15% glycerol) for 1 minute followed by washing 2 times with PBS. Medium was replaced with DMEM containing oligonucleotide at the original concentration. Cells were incubated for 48 hours and harvested. Cell lysates were analyzed for chloramphenicol acetyl transferase by standard procedures. Acetylated and nonacetylated $^{14}$C-chloramphenicol were separated by thin layer chromatography and quantitated by liquid scintillation. The results are expressed as percent acetylation.

Two lots of the positive control compound were found to acetylate at a level of 29% and 30%. The negative controls, test compounds five, six and seven, were found to acetylate at 59%, 58% and 47%, respectively. The 3'-cholic acid conjugate test compound, Oligomer 3, was found to acetylate to 23%, the 5'-cholic acid conjugate test compound, Oligomer 2, was found to acetylate to 36% and the test compound conjugated at both the 3'-end and the 5'-end, Oligomer 5, was found to acetylate to 27%.

The results of this test suggests that placement of a cholic acid moiety at the 3'-terminus of an oligonucleotide increase the activity. This in turn suggests that the increased activity was the result of increased cellular membrane transport.

Procedure D

Determination of Cellular Uptake Judged By Inhibition of pHIVluc with Cholic Acid Linked 2'-O-Methyl Substituted Oligonucleotides For this test the absence of an oligonucleotide in a test well served as the control. All oligonucleotides were tested as 2'-O-methyl analogs. For this test an oligonucleotide of the sequence:

Oligomer 43 (SEQ ID NO:10): CCC AGG CUC AGA where each of the nucleotides of the oligonucleotide includes a 2'-O-methyl substituent group served as the basic test compound. The second test compound of the sequence:

Oligomer 44: 5'-CHA CCC AGG CUC AGA wherein CHA represents cholic acid and where each of the nucleotides of the oligonucleotide includes a 2'-O-methyl substituent group, was also of the same sequence as the first test compound. This second test compound included cholic acid conjugated to its 5'-end and was prepared as per the method of Example 3 in application Ser. No. 782,374 utilizing 2'-O-methyl phosphoramidite intermediates as identified in Example 1(C). The third test compound of the sequence:

Oligomer 45: CCC AGG CUC AGA 3'-CHA wherein CHA represents cholic acid and where each of the nucleotides of the oligonucleotide includes a 2'-O-methyl substituent group was also of the same sequence as the first test compound. The third test compound included cholic acid conjugated to its 3'-end and was prepared as per the method of Example 4 in application Ser. No. 782,374 utilizing 2'-O-methyl phosphoramidite intermediates as identified in Example 1(C). The fourth test compound was a 2'-O-Me oligonucleotide of a second sequence:

Oligomer 46 (SEQ ID NO:11): GAG CUC CCA GGC where each of the nucleotides of the oligonucleotide includes a 2'-O-methyl substituent group. The fifth test compound was of sequence:

Oligomer 47: 5'-CHA GAG CUC CCA GGC wherein CHA represents cholic acid and where each of the nucleotides of the oligonucleotide includes a 2'-O-methyl substituent group. It was of the same sequence as the fifth test compound. This test compound included cholic acid conjugated to its 5'-end and was prepared as per the method of Example 3 in application Ser. No. 782,374 utilizing 2'-O-methyl phosphoramidite intermediates as identified in Example 1(C).

A sixth test compound was a randomized oligonucleotide of the sequence:

Oligomer 48 (SEQ ID NO:12): CAU GCU GCA GCC.

HeLa cells were seeded at 4×10$^5$ cells per well in 6-well culture dishes. Test oligonucleotides were added to triplicate wells at 1 µM and allowed to incubate at 37° C. for 20 hours. Medium and oligonucleotide were then removed, cells washed with PBS and the cells were CaPO$_4$ transfected. Briefly, 5 µg of pHIVluc, a plasmid expressing the luciferase cDNA under the transcriptional control of the HIV LTR constructed by ligating the KpnI/HindIII restriction fragments of the plasmids pT3/T7luc and pHIVpap (NAR 19(12)) containing the luciferase cDNA and the HIV LTR respectively, and 6 µg of pcDEBtat, a plasmid expressing the HIV tat protein under the control of the SV40 promoter, were added to 500 µl of 250 mM CaCl$_2$ then 500 µl of 2×HBS was added followed by vortexing. After 30 minutes, the CaPO$_4$ precipitate was divided evenly between the six wells of the plate, which was then incubated for 4 hours. The media and precipitate were then removed, the cells washed with PBS, and fresh oligonucleotide and media were added. Incubation was continued overnight. Luciferase activity was determined for each well the following morning. Media was removed, then the cells washed 2× with PBS. The cells were then lysed on the plate with 200 µl of LB (1% Trit X-100, 25 mM Glycylglycine pH 7.8, 15 mM MgSO$_4$, 4 mM EGTA, 1 mM DTT). A 75 µl aliquot from each w ll was then added to a well of a 96 well plate along with 75 µl of assay buffer (25 mM Glycylglycine pH 7.8, 15 mM MgSO$_4$, 4 mM EGTA, 15 mM KPO$_4$, 1 mM DTT, 2.5 mM ATP). The plate was then read in a Dynatec multiwell luminometer that injected 75 µl of Luciferin buffer (25 mM Glycylglycine pH 7.8, 15 mM MgSO$_4$, 4 mM EGTA, 4 mM DTT, 1 mM luciferin) into each well, immediately reading the light emitted (light units).

The random sequence compound (Oligomer 48) and the other non-cholic acid-conjugated test compounds (Oligomers 43 and 46) had comparable activity. The 5'-conjugate of the first sequence (Oligomer 44) also had activity comparable to the non-conjugated compounds. The 5'-conjugate of the second sequence (Oligomer 47) showed a three-fold increase in activity compared to the non-conjugated compounds and the 3'-conjugate of the first sequence (Oligomer 45) showed a further 3-fold increase in activity compared to Oligomer 47.

All the test cholic acid-bearing oligonucleotides showed significant inhibition of luciferase production compared to non-cholic acid-bearing oligonucleotides. This suggests that the increased activity was the result of increased cellular membrane transport of the cholic acid-bearing test oligonucleotides.

EXAMPLE 3

Preparation of 5'-O-[Dim thoxytrityl]-2'-O-[hexyl-(Ω-N-phthalimido)amino]uridine and 5'-O-[dimethoxytrityl]-3'-O-[hexyl(Ω-N-phthalimidoamino)uridine.

2',3'-O-Dibutyl stannylene-uridine was synthesized according to the procedure of Wagner et. al., *J. Org. Chem.*, 1974, 39, 24. This compound was dried over $P_2O_5$ under vacuum for 12 hours. To a solution of this compound (29 g, 42.1 mmols) in 200 ml of anhydrous DMF were added (16.8 g, 55 mmols) of 6-bromohexyl phthalimide and 4.5 g of sodium iodide and the mixture was heated at 130° C. for 16 hours under argon. The reaction mixture was evaporated, co-evaporated once with toluene and the gummy tar residue was applied on a silica column (500 g). The column was washed with 2 L of ethyl acetate (EtOAc) followed by eluting with 10% methanol (MeOH):90% EtOAc. The product, 2'- and 3'-isomers of O-hexyl-Ω-N-phthalimido uridine, eluted as an inseparable mixture ($R_f$=0.64 in 10% MEOH in EtoAc). By $^{13}C$ NMR, the isomeric ration was about 55% of the 2' isomer and about 45% of the 3'isomer. The combined yield was 9.2 g (46.2%). This mixture was dried under vacuum and re-evaporated twice with pyridine. It was dissolved in 150 mL anhydrous pyridine and treated with 7.5 g of dimethyocytrityl chloride (22.13 mmols) and 500 mg of dimethylaminopyridine (DMAP). After 2 hour, thin layer chromatography (TLC; 6:4 EtOAc:Hexane) indicated complete disappearance of the starting material and a good separation between 2' and 3' isomers ($R_f$=0.29 for the 2' isomer and 0.12 for the 3' isomer). The reaction mixture was quenched by the addition of 5 mL of $CH_3OH$ and evaporated under reduced pressure. The residue was dissolved in 300 mL $CH_2Cl_2$, washed successively with saturated $NaHCO_3$ followed by saturated NaCl solution. It was dried over $Mg_2SO_4$ and evaporated to give 15 g of a brown foam which was purified on a silica gel (500 g) to give 6.5 g of the 2'-isomer and 3.5 g of the 3' isomer.

EXAMPLE 4

Preparation of 5'-O-Dimethoxytrityl-2'-O-[hexzyl-(Ω-N-phthalimido)amino]uridine-3'-O-(2-cyanoethyl-N,N-diisopropyl)-phosphoramidite The 5'-dimethoxytrityl-2'-[O-hexyl-(Ω-N-phthalimido)-amino]uridine (4 g, 5.2 mmole) was dissolved in 40 mL of anhydrous $CH_2Cl_2$. To this solution diisopropylaminetetrazolide (0.5 g, 2.9 mmol) was added and stirred overnight. TLC (1:1 EtOAC/hexane) showed complete disappearance of starting material. The reaction mixture was transferred with $CH_2Cl_2$ and washed with saturated $NaHCO_3$ (100 mL) followed by saturated NaCl solution. The organic layer was dried over anhydrous $Na_2SO_4$ and evaporated to yield 6.4 g of a crude product which was purified in a silica column (200 g) using 1:1 hexane/EtOAc to give 4.6 g (4.7 mmol, 90%) of the desired phosphoramidite.

EXAMPLE 5

Preparation of 5'-O-(Dimethoxytrityl)-3'-O-[hexyl-(Ω-N-phthalimido) amino]uridine-2'-O-succinyl-aminopropyl controlled pore glass Succinylated and capped aminopropyl controlled pore glass (CPG; 500 Åpore diameter, aminopropyl CPG, 1.0 grams prepared according to Damha et. al., *Nucl. Acids Res.* 1990, 18, 3813.) was added to 12 ml anhydrous pyridine in a 100 ml round-bottom flask. 1-(3-Dimethylaminopropyl)-3-ethyl-carbodiimide (DEC; 0.38 grams, 2.0 mmol)], triethylamine (TEA; 100 μl, distilled over $CaH_2$), dimethylaminopyridine (DMAP; 0.012 grams, 0.1 mmol) and nucleoside 5'-O-dimethoxytrityl-3'-O-[hexyl-(Ω-N-phthalimidoamino)]uridine (0.6 grams, 0.77 mmol) were added under argon and the mixture shaken mechanically for 2 hours. More nucleoside (0.20 grams) was added and the mixture shaken an additional 24 hours. CPG was filtered off and washed successively with dichloromethane, triethylamine, and dichloromethane. The CPG was then dried under vacuum, suspended in 10 ml piperidine and shaken 15 minutes. The CPG was filtered off, washed thoroughly with dichloromethane and again dried under vacuum. The extent of loading (determined by spectrophotometric assay of dimethoxytrityl cation in 0.3 M p-toluenesulfonic acid at 498 nm) was approximately 28 μmol/g. The 5'-O-(dimethoxytrityl)-3'-O-[hexyl-(Ω-N-phthalimidoamino]uridine-2'-O-succinyl-aminopropyl controlled pore glass was used to synthesize the oligomers 5'-GACU*-3' and 5'-GCC TTT CGC GAC CCA ACA CU*-3' (SEQ ID NO:13) (where the * indicated the derivatized nucleotide) in an ABI 380B DNA synthesizer using phosphoramidite chemistry standard conditions. 45 and 200 O.D.'s of the 4-mer and 20-mer, respectively, were obtained from two and three 1 μmol syntheses after purification by RP-HPLC and desalting.

The oligomer 5'-GACU*-3' was used to confirm the structure of 3'-O-hexylamine tether introduced into the oligonucleotide by NMR. As expected a multiplet signal was observed between 1.0–1.8 ppm in $^1H$ NMR. The oligomer 5'-GCC TTT CGC GAC CCA ACA CU*-3' belongs to a HCV sequence and it was used to show the nuclease resistance properties of the 3'-O-amino tether [see example 38].

EXAMPLE 6

Preparation of 5'-O-(Dimethoxytrityl)-2'-O-[hexyl-(Ω-N-phthalimido)amino]3'-O-succinyl-aminopropyl controlled pore Glass The procedure of Example 5 was repeated, except that 5'-O-(Dimethoxytrityl)-2'-O-[hexyl-(Ω-N-phthalimidoamido)-amino]uridine was used in the loading process.

EXAMPLE 7

Preparation of 5'-O-(Dimethoxytrityl)-2'-O-(hexylamino)-uridine

5'-O-(dimethoxytrityl)-2'-O-[hexyl-(Ω-N-phthalimido amino)]uridine (4.5 grams, 5.8 mmol) was dissolved in 200 ml methanol in a 500 ml flask. Hydrazine (1 ml, 31 mmol) was added to the stirring reaction mixture. The mixture was heated to 60–65° in an oil bath and refluxed 14 hours.

Solvent was evaporated in vacuo. The residue was dissolved in dichloromethane (250 ml) and extracted twice with an equal volume $NH_4OH$. The organic layer was evaporated to yield 4.36 grams of crude product, and NMR indicated that the product was not completely pure. $R_f$=0 in 100% ethyl acetate. The product was used in subsequent reactions without further purification.

EXAMPLE 8

Preparation of 5'-O-(dimethoxytrityl)-3'-O-[hexylamino] uridine

The procedure of Example 7 was repeated, except that 5'-O-(dimethoxytrityl)-3'-O-[hexyl-(Ω-N-phthalimidoamino)] uridine was used as the starting material.

EXAMPLE 9

Preparation of 5'-O-(dimethoxytrityl)-2'-O-[hexyl-N-(1-pyrene propyl carbonyl)amino]uridine 5'-O-Dimethoxytrityl-2'-O-(hexylamino)uridine (0.5 g, 0.78 mmol) was dissolved in anhydrous DMF (15 mL). 1-Hydroxybenzotriazole (0.16 grams, 1.17 mmol) and 1-pyrene-butyric acid pentafluorophenyl ester (0.53 grams, 1.17 mmol) were added to the reaction mixture. The mixture was stirred under argon at room temperature for 2 hours, after which it was concentrated in vacuo. Residual DMF was coevaporated with toluene. The residue was dissolved in dichloromethane (50 mL) and washed with an equal volume saturated $NaHCO_3$. The aqueous layer was washed with dichloromethane and the combined organic extracts washed with an equal volume saturated NaCl. The aqueous layer was washed with dichloromethane and the combined organic layers dried over $MgSO_4$ and concentrated. The residue was chromatographed on a silica gel column, eluting with a gradient of 50% ethyl acetate in hexanes to 100% ethyl acetate. The desired product (0.83 grams, 58%) eluted with 100% ethyl acetate ($R_f$ 0.46 by thin-layer chromatography (TLC)).

EXAMPLE 10

Preparation of 5'-O-[Dimethoxytrityl]-2'-O-[hexyl-N-(1-pyrene propyl carbonyl)amino]uridine-3'-O-(2-cyanoethyl-N, N-diisopropyl)phosphoramidite 5'-O-[Dimethoxytrityl]-2'-O-[hexyl-N-(1-pyrene propyl carbonyl)amino] uridine (0.80 grams, 0.87 mmol) was dissolved in 20 mL dry dichloromethane. 2-Cyanoethyl N,N,N',N'-tetraisopropylphosphorodiamidite (purchased from Sigma Chemical Co; 800 µL, 2.4 mmol) and diisopropylamine tetrazolide (0.090 grams, 0.52 mmol) were added to the mixture, which was stirred under argon for 20 hours The reaction mixture was then concentrated in vacuo and the residue dissolved in dichloromethane (75 mL). The solution was washed with an equal volume of saturated $NaHCO_3$. The aqueous layer was washed with dichloromethane (20 mL) and the combined organic layers washed with an equal volume of saturated NaCl. The aqueous layer was washed with dichloromethane (20 mL) and the combined organic layers dried over $MgSO_4$ and concentrated. The residue was chromatographed on a silica gel column, eluting with a gradient of 50% ethyl acetate in hexanes to 100% ethyl acetate. The desired product (750 mg, 78% yield, $R_f$ 0.54 by TLC in 100% ethyl acetate) eluted with 100% ethyl acetate.

EXAMPLE 11

Preparation of 2'-O-[hexyl-N-(1-pyrene-propyl-carbonyl) amino] uridine

5'-O-dimethoxytrityl-2'-O-[hexyl-N-(1-pyrene-propyl-carbonyl)amino]uridine (1.0 g) was dissolved in 20 mL $CH_2Cl_2$ and kept in ice-bath for 10 minutes. To the cold solution, 5 mL of 80% acetic acid in water was added and the solution was left to stand for 30 minutes. It was then evaporated to dryness and loaded into a silica column and eluted with 10% methanol in methylene chloride to give 2'-O-[hexyl-N-(1-pyrene-propyl-carbonyl)amino]uridine.

EXAMPLE 12

Preparation of 5'-O-(dimethoxytrityl)-2'-O-[hexyl-N-(1-pyrene propylcarbonyl amino]uridine-3'-O-[succinylaminopropyl]-controlled pore glass Succinylated/capped aminopropyl controlled pore glass was dried under vacuum for 3 hours immediately before use. A portion (0.3 g) was added to 3 ml anhydrous pyridine in a 50 ml round-bottom flask. DEC (0.12 grams, 0.63 mmol), TEA (25 µl, distilled over $CaH_2$), DMAP (0.005 grams, mmol) and 5'-O-(dimethoxytrityl)-3'-O-[hexyl-N-(1-pyrene propyl carbonyl] amino]uridine (0.21 grams, 0.22 mmol) were added under argon and the mixture shaken mechanically for 19 hours. More nucleoside (0.025 grams) was added and the mixture shaken an additional 5.5 hours. Pentachlorophenol (0.045 grams, mmol) was added and the mixture shaken 18 hours. CPG was filtered off and washed successively with dichloromethane, triethylamine, and dichloromethane. The resulting CPG was then dried under vacuum, suspended in 15 ml piperidine and shaken 30 minutes. CPG was filtered off, washed thoroughly with dichloromethane and again dried under vacuum. The extent of loading (determined by spectrophotometric assay of dimethoxytrityl cation in 0.3 M p-toluenesulfonic acid at 498 nm) was approximately 27 µmol/g. The product solid support was subsequently used to synthesize the oligomers.

EXAMPLE 13

Preparation of 5'-O-dimethoxytrityl-3'-O-[hexyl-N-(1-pyrene propyl carbonyl]amino]uridine-2'-O-(succinyl amino propyl) controlled pore glass The procedure of Example 12 is repeated, except that 5'-O-dimethoxytrityl-3'-O-[hexyl-N-(1-pyrenepropylcarbonyl) amino]uridine is used.

EXAMPLE 14

Preparation of 5'-O-(dimethoxytrityl)-2'-O-[hexyl-N-(5-thio carbonyl-3,6-dipivolyl-fluorescein)amino] uridine Fluorescein isothiocyanate (Isomer I, available from Cal Biochem, La Jolla, Calif.) was treated with 12 equivalents of pivolyl chloride in $Et_3N/THF$ to give di-O-pivolyl fluorescein isothiocyanate. This compound was purified in silica gel column using 3:1 hexane:ethyl acetate. Nucleoside 5'-O-(dimethoxytrityl)-2'-O-(hexylamino)uridine was then condensed with dipivolyl fluorescein isothiocyanate in $CH_2Cl_2$/pyrimidine. The resultant compound 5'-O-(dimethoxytrityl)-2'-O-[hexyl-N-(5-thiocarbonyl-3,6-dipivolyl-fluorescein)amino]uridine is then purified by using 100% ethyl acetate, in a silica column.

EXAMPLE 15

Preparation of 5'-O-dimethoxytrityl-2'-O-[hexyl-N-(5-thiocarbonyl-3,6-di-pivolyl fluorescein)amino] uridine-3'-O-(2-cyanoethyl, N-N-diisopropyl phosphoramidite 5'-O-(dimethoxytrityl)-2'-O-[hexyl-N-(5-thiocarbonyl-3, 6-dipivolyl fluorescein)amino]uridine (0.75 grams, 0.672 mmol) was dissolved in dry dichloromethane (20 mL). 2-Cyanoethyl N,N,N',N'-tetraisopropylphosphorodiamidite (700 µL, 2.2 mmol) and diisopropylamine tetrazolide were added to the mixture, which was stirred under argon for 16 hours. The reaction mixture was then concentrated in vacuo and the residue dissolved in dichloromethane (75 mL) followed by washing with an equal volume of saturated $NaHCO_3$. The aqueous layer was washed with dichloromethane (50 mL) and the combined organic layers washed with an equal volume of saturated NaCl. The aqueous layer was washed with dichloromethane (50 mL) and the combined organic layers dried over $MgSO_4$ and concentrated.

The residue was chromatographed on a silica gel column, eluting with a gradient of 25% ethyl acetate in hexanes to 100% ethyl acetate. The desired product (670 mg, 77% yield, $R_f$ 0.79 by TLC) eluted with 100% ethyl acetate.

EXAMPLE 16

Preparation of 5'-O-(dimethoxytrityl)-2'-O-[hexyl-N-(5-thiocarbonyl-3,6-di-pivolyl fluorescein)amino] uridine-3'-O-(succinylaminopropyl) controlled pore glass.

Succinylated and capped aminopropyl controlled pore glass (CPG) is dried under vacuum for 3 hours immediately before use. CPG (0.3 grams) is added to 3 ml anhydrous pyridine in a 50 ml round-bottom flask. DEC (0.12 grams, 0.63 mmol), TEA (25 µl, distilled over $CaH_2$, DMAP (dimethyl amino pyridine) (0.005 grams, 0.04 mmol) and 5'-O-dimethoxytrityl-2'-O-[hexyl-N-(5-thiocarbonyl-3,6-di-pivolyl fluorescein)amino]uridine (0.21 grams, 0.19 mmol) are added under argon and the mixture shaken mechanically for 19 hours. More nucleoside (0.025 grams) is added and the mixture shaken an additional 5.5 hours. Pentachlorophenol (0.045 grams, 0.17 mmol) is added and the mixture shaken 18 hours. CPG is filtered off and washed successively with dichloromethane, triethylamine, and dichloromethane. CPG then is dried under vacuum, suspended in 15 mL piperidine and shaken 30 minutes. CPG is filtered off, washed thoroughly with dichloromethane, and again dried under vacuum. The extent of loading is then determined by spectrophotometric assay of dimethoxytrityl cation in 0.3 M p-toluenesulfonic acid at 498 nm.

EXAMPLE 17

Preparation of 5'-O-(dimethoxytrityl)-2'-O-[hexyl-N-(5-ozycarbonyl-cholesteryl)amino]uridine.

Nucleoside 5'-O-(dimethoxytrityl)-2'-O-[hexylamino]-uridine (3.85 g, 6.0 mmol) was dissolved in anhydrous pyridine/dichloromethane 50/50 (v/v) (20 mL). Cholesteryl chloroformate (Fluka, 3.0 g, 6.68 mmol) was dissolved in anhydrous dichloromehthane (20 ml) and added slowly under argon with a syringe to the stirring reaction mixture. The mixture was stirred under argon at room temperature for 2 h after which it was concentrated in vacuo. Residual DMF was coevaporated with toluene. The residue was dissolved in dichloromethane (50 mL) and washed with an equal volume saturated $NaHCO_3$. The aqueous layer was washed with dichloromethane and the combined organic extracts washed with an equal volume saturated Nacl. The aqueous layer was washed with dichloromethane and the combined organic layers dried over $MgSO_4$ and concentrated. The residue was chromatographed on a silica gel column with a gradient of 25% ethyl acetate in hexanes to 100% ethyl acetate. The desired product (3.78 g, 60%) eluted with 100% ethyl acetate ($R_f$ 0.41 by TLC).

EXAMPLE 18

Preparation of 5'-O-(dimethoxytrityl)-2'-O-[hexyl-N-(3-oxy-carbonyl-cholesteryl)amino]uridine-3'-O-[2-cyanoethyl-N,N-di-isopropyl]phosphoramidite Nucleoside 5'-O-(dimethoxytrityl)-2'-O-[hexyl-N-(3-oxycarbonyl-cholesteryl)amino]uridine (3.44 g, 3.3 mmol) was dissolved in dry dichloromethane (75 mL). 2-cyanoethyl N,N,N'N'-tetraisopropylphosphorodiamidite (Sigma, 2.1 ml, 6.6 mmol) and diisopropylamine tetrazolide (0.29 g, 1.7 mmol) were added to the mixture, which was stirred under argon for 16 H. Dichloromethane (75 mL) was added to the solution, which was washed with an equal volume of saturated $NaHCO_3$. The aqueous layer was washed with an equal volume of dichloromethane. The aqueous layer was washed with dichloromethane (30 ml) and the combined organic layers washed with an equal volume of saturated NaCl. The aqueous layer was washed with dichloromethane (30 mL) and the combined organic layers dried over $Mg_2SO_4$ and concentrated in vacuo. The residue was chromatographed on a silica gel column with a gradient of 25% ethyl acetate in hexanes to 70% ethyl acetate. The desired product (3.35 g, 82% yield, $R_f$=0.71 by TLC in 50% ethyl acetate in hexanes) eluted with 50% ethyl acetate.

EXAMPLE 19

Preparation of 5'-O-(dimethoxytrityl)-2'-O-[hexyl-N-(3-ozycarbonyl-cholesteryl)amino]uridine-3'-O-(succinyl aminopropyl)-controlled pore glass.

Succinylated and capped controlled pore glass (0.3 grams) is added to 2.5 ml anhydrous pyridine in a 15 ml pear-shaped flask. DEC (0.07 grams, 0.36 mmol), TEA (100 µl, distilled over $CaH_2$), DMAP (0.002 grams, 0.016 mmol) and 5'-O-(dimethoxytrityl)-2'-O-[hexyl-N-(3-oxycarbonyl-cholesteryl)-amino]uridine (0.25 grams, 0.23 mmol) are added under argon and the mixture shaken mechanically for 16 hours. More nucleoside (0.20 grams) is added and the mixture shaken an additional 18 hours. Pentachlorophenol (0.03 grams, 0.11 mmol) is added and the mixture shaken 9 hours. CPG is filtered off and washed successively with dichloromethane, triethylamine, and dichloromethane. CPG is then dried under vacuum, suspended in 10 ml piperidine and shaken 15 minutes. CPG is filtered off, washed thoroughly with dichloromethane and again dried under vacuum. The extent of loading is determined by spectrophotometric assay of dimethoxytrityl cation in 0.3 M p-toluenesulfonic acid at 498 nm as approximately 39 µmol/g.

EXAMPLE 20

Preparation of 5'-O-(dimethoxytrityl)-2'-O-[hexyl-N-(2,4-dinitrophenyl) amino]uridine.

5'-O-(dimethoxytrityl)-2'-O-(hexylamino)uridine (0.88 grams, 1.37 mmol) was dissolved in methanol (20 mL). 2,4-Dinitrofluorobenzene (DNFB, 0.25 grams, 1.37 mmol) was added and the mixture shaken on a mechanical shaker. The reaction was monitored by TLC. After 90 min, another 0.25 grams of DNFB was added and the reaction mixture shaken an additional 30 min, followed by addition of another 0.25 grams of DNFB. After shaking 2.5 hours, the mixture was concentrated in vacuo and chromatographed on a silica gel column, eluting with a gradient of 25% ethyl acetate in hexanes to 100% ethyl acetate. The desired product (0.51 grams, 46%) eluted with 100% ethyl acetate ($R_f$ 0.85 by TLC).

EXAMPLE 21

Preparation of 5'-O-(dim thoxytrityl)-2'-O-[hexyl-N-(2,4-dinitrophenyl)amino]uridine-3'-O-(2-cyanoethyl-N,N-diisopropyl)phosphoramidite.

5'-O-(dimethoxytrityl)-2'-O-[hexyl-N-(2,4-dinitrophenyl) amino]uridine (0.45 grams, 0.55 mmol) was dissolved in dry dichloromethane (12 mL). 2-Cyanoethyl N,N,N',N'-tetraisopropylphosphorodiamidite (380 µL, 1.2 mmol) and diisopropylamine tetrazolide (0.041 grams, 0.024 mmol) were added to the mixture, which was stirred under argon for 16 hours. The reaction mixture was then concentrated in vacuo and the residue dissolved in dichloromethane (75 mL) followed by washing with an equal volume of saturated NaHCO$_3$. The aqueous layer was washed with dichloromethane (25 mL) and the combined organic layers washed with an equal volume of saturated NaCl. The aqueous layer was washed with dichloromethane (25 mL) and the combined organic layers dried over MgSO$_4$ and concentrated. The residue was chromatographed on a silica gel column, eluting with a gradient of 20% ethyl acetate in hexanes to 100% ethyl acetate. The desired product (510 mg foam, 93% yield, R$_f$ 0.70 by TLC) eluted with 100% ethyl acetate. $^{31}$PNMR (CDCl$_3$): 150.56 and 150.82 ppm.

EXAMPLE 22

Preparation of 5'-O-(dimethoxytrityl)-2'-O-[h xyl-N-(2,4-dinitrophenyl)amino]uridine-3'-O-(succinyl aminopropyl) controlled pore glass Succinylated and capped controlled pore glass (0.3 grams) is added to 3 ml anhydrous pyridine in a 50 ml round-bottom flask. DEC (0.12 grams, mmol), TEA (25 µl, distilled over CaH$_2$), DMAP (0.005 grams, 0.041 mmol) and 5'-O-(dimethoxytrityl) -2'-O-[hexyl-N-(2,4-dinitrophenyl) amino]uridine (0.21 grams, 0.26 mmol) are added under argon and the mixture shaken mechanically for 19 hours. More nucleoside (0.025 grams) is added and the mixture shaken an additional 5.5 hours. Pentachlorophenol (0.045 grams, 0.16 mmol) is added and the mixture shaken 18 hours. CPG is filtered off and washed successively with dichloromethane, triethylamine, and dichloromethane. CPG then is dried under vacuum, suspended in 15 ml piperidine and shaken for 15 minutes. CPG is filtered off, washed thoroughly with dichloromethane, and again dried under vacuum. The extent of loading is determined by spectrophotometric assay of dimethoxytrityl cation in 0.3 M p-toluenesulfonic acid at 498 nm, as approximately 29 µmol/gm.

EXAMPLE 23

Preparation of 5'-O-(dimethoxytrityl)-2'-O-[hexyl-N-(Nα-Nimid-Di-FMOC-L-Histidyl)amino]uridine Nucleoside 5'-O-(dim thoxytrityl)-2'-O-(hexylamino)-uridine (0.97 g, 1.51 mmol) was dissolved in dichloromethane (25 mL) and cooled to 0° C. in an ice bath. Nα,Nimid-Di-FMOC-L-histine pentafluorophenyl ester (2.4 g, 3.1 mmol, purchased from Sigma) and 1-hydroxybenzotriazole (0.32 g, 0.24 mmol, purchased from Fluka) were added to the stirred reaction mixture stirred under argon. After 15 minutes, the ice bath was removed and the mixture stirred under argon at room temperature for 72 h. The mixture was concentrated in vacuo and chromatographed on a silica gel column, eluting with a gradient of 50% ethyl acetate in hexanes to 70% ethyl acetate in hexanes. The desired product (0.53 g, 28%) eluted with 70% ethyl acetate (R$_f$ 0.53 by TLC in 100% ethyl acetate).

EXAMPLE 24

Preparation of 5'-O-(dimethoxytrityl)-2'-O-[hexyl-N-(Nα-Nimid-Di-FMOC-L-histidyl)-amino]-uridine-3'-O-[2-cyanoethyl-N,N-diisopropyl] phosphoramidite.

5'-O-Dimethoxytrityl-2'-O-[hexyl-N-(Nα-Nimid-Di-FMOC-L-histidyl)amino]uridine (1.9 g, 1.6 mmol) is dissolved in dry dichloromethane (20 mL). 2-Cyanoethyl N,N,N',N'-tetraisopropylphosphorodiamidite (800 µL, 2.4 mmol) and diisopropylamine tetrazolide (0.090 grams, 0.52 mmol) are added to the mixture, which is stirred under argon for 20 hours. The reaction mixture then is concentrated in vacuo and the residue dissolved in dichloromethane (75 mL). The solution is washed with an equal volume of saturated NaHCO$_3$. The aqueous layer is washed with dichloromethane (20 mL) and the combined organic layers washed with an equal volume of saturated NaCl. The aqueous layer is washed with dichloromethane (20 mL) and the combined organic layers dried over MgSO$_4$ and concentrated. The residue is chromatographed on a silica gel column, eluting with a gradient of 50% ethyl acetate in hexanes to 100% ethyl acetate. The desired product elutes with 100% ethyl acetate.

EXAMPLE 24

Preparation of 5'-O-(dimethoxytrityl)-2'-O-[hexyl-N-(Nα-Nimid-Di-FMOC)-L-histidyl)amino]uridine-3'-O-[succinylaminopropyl] controlled pore glass Succinylated and capped controlled pore glass (dried under vacuum for 3 hours immediately before use; 0.3 grams) is added to 3 ml anhydrous pyridine in a 50 ml round-bottom flask. DEC (0.12 grams, 0.63 mmol), TEA (25 µl, distilled over CaH$_2$), DMAP (0.005 grams, 0.04 mmol) and 5'-O-(dimethoxytrityl)-2'-O-[hexyl-N-(Nα-Nimid-Di-FMOC)-L-histidyl)amino]-uridine (0.21 grams, 0.17 mmol) are added under argon and the mixture shaken mechanically for 19 hours. More nucleoside (0.025 grams) is added and the mixture shaken an additional 5.5 hours. Pentachlorophenol (0.045 grams, 0.17 mmol) is added and the mixture shaken 18 hours. CPG is filtered off and washed successively with dichloromethane, triethylamine, and dichloromethane. CPG then is dried under vacuum, suspended in 15 ml piperidine and shaken 15 minutes. CPG is filtered off, washed thoroughly with dichloromethane and again dried under vacuum. The extent of loading is determined by spectrophotometric assay of dimethoxytrityl cation in 0.3 M p-toluenesulfonic acid at 498 nm. to be approximately 27 µmol/g.

EXAMPLE 25

Pr paration of 5'-O-(dimethoxytrityl)-2'-O-[hexyl-N-(Ω-m thyl-polyethylene glycol-propionoyl)amino] uridine Nucleoside 5'-O-(dimethoxytrityl)-2'-O-[hexylamino]-uridine, (1 g, 1.55 mmol) is dissolved in anhydrous DMF (15 mL). 1-Hydroxybenzotriazole (0.24 g, 1.75 mmol) and polyethylene glycol-propionic acid-NHS-ester (1.23 g, 1.75 mmol) are added to the reaction mixture. The mixture is stirred under argon at room temperature for 2 hours after which it is concentrated in vacuo. Residual DMF is coevaporated with toluene. The residue is dissolved in dichloromethane (50 mL) and then washed with an equal volume saturated NaHCO$_3$. The aqueous layer is washed with dichloromethane and the combined organic extracts washed with an equal volume saturated NaCl. The aqueous layer is washed with dichloromethane and the combined organic layers dried over MgSO$_4$ and concentrated. The residue is chromatographed on a silica gel column, eluting with a gradient of 50% ethyl acetate in hexanes to 100% ethyl acetate. The desired product (1.08 g, 58%) eluted with 100% ethyl acetate.

EXAMPLE 26

Preparation of 5'-O-(dimethoxytrityl)-2'-O-[hexyl-N-(Ω-methyl-polyethylene glycol-propionoyl) amino]uridine-3'-O-(2-cyano-ethoxy-N,N-diisopropyl)phosphoramidite 5'-O-(Dimethoxytrityl)-2'-O-[hexyl-N-(Ω-methyl-polyethylene glycol-propionoyl)amino]uridine (1.04 grams, 0.87 mmol) is dissolved in dry dichloromethane (20 mL). 2-Cyano-ethyl N,N,N',N'-tetraisopropylphosphorodiamidite (800 μL, 2.4 mmol) and diisopropylamine tetrazolide (0.090 grams, 0.52 mmol) are added to the mixture, which is stirred under argon for 20 hours. The reaction mixture then is concentrated in vacuo and the residue dissolved in dichloromethane (75 mL). The solution is washed with an equal volume of saturated NaHCO$_3$. The aqueous layer is washed with dichloromethane (20 mL) and the combined organic layers washed with an equal volume of saturated NaCl. The aqueous layer is washed with dichloromethane (20 mL) and the combined organic layers dried over MgSO$_4$ and concentrated. The residue is chromatographed on a silica gel column, eluting with a gradient of 50% ethyl acetate in hexanes to 100% ethyl acetate. The desired product elutes with 100% ethyl acetate.

EXAMPLE 27

Preparation of 5'-O-(dimethoxytrityl)-2'-O-[hexyl-N-(Ω-methyl-polyethylene glycol-propionoyl) amino]uridine-3'-O-(succinyl-aminopropyl) controlled pore glass Succinylated and capped controlled pore glass (CPG) is dried under vacuum for 3 hours immediately before use. Controlled pore glass (0.3 grams) is added to 3 ml anhydrous pyridine in a 50 ml round-bottom flask. DEC (0.12 grams, 0.67 mmol), TEA (25 μl, distilled over CaH$_2$), DMAP (0.005 grams, mmol) and 5'-O-(dimethoxytrityl)-2'-O-[hexyl-N-(w-methyl-polyethylene glycol-propionoyl)amino]uridine (0.21 grams, 0.175 mmol) are added under argon and the mixture shaken mechanically for 19 hours. More nucleoside (0.025 grams) is added and the mixture shaken an additional 5.5 hours. Pentachlorophenol (0.045 grams, 0.17 mmol) is added and the mixture shaken 18 hours. CPG is filtered off and washed successively with dichloromethane, triethylamine, and dichloromethane. CPG then is dried under vacuum, suspended in 15 ml piperidine, and shaken 15 minutes. CPG is filtered off, washed thoroughly with dichloromethane, and again dried under vacuum. The extent of loading is determined by spectrophotometric assay of dimethoxytrityl cation in 0.3 M p-toluenesulfonic acid at 498 nm. to be approximately 18 μmol/g.

EXAMPLE 28

Preparation of Macrocycle Derivatized Nucleoside

5'-O-(dimethoxytrityl)-2'-O-(hexylamine)uridine is treated as per the procedure of Example 3 with the macrocycle 4-{1,4,8,11-tetraza-[tri-(trifluoroacetyl)cyclotetradec-1-yl]}methyl benzoic acid-N-hydroxy succinimide ester (prepared according to Simon Jones, et. al., *Bioconjugate Chem*. 1991, 2, 416) to yield the product.

EXAMPLE 29

Preparation of Macrocycle Derivatized Uridine Phosphoramidite

The nucleoside product of Example 28 is treated as per the procedure of Example 4 to yield the product.

EXAMPLE 30

Preparation of CPG Derivatized with Macrocycl D rivatiz d Nucleoside

The nucleoside product of Example 28 is treated as per the procedure of Example 5 to yield the product.

EXAMPLE 31

Preparation of 5'-O-(dimethoxyltrityl)-2'-O-(hexyl-N-(folate)-amino)uridine

5'-O-(Dimethoxytrityl)-2'-O-(hexylamine)uridine is treated as per the procedure of Example 3 with folic acid pentafluorophenyl ester (protected with an isobutyryl protecting group) to yield the product.

EXAMPLE 32

Preparation of 5'-O-(dimethoxyltrityl)-2'-O-[hexyl-N-(folate)-amino]uridine-3'-O-(2-cyanoethoxy-N,N-diisopropyl)phosphoramidite The nucleoside product of Example 28 is treated as per the procedure of Example 4 to yield the product.

EXAMPLE 33

Preparation of CPG derivatized with 5'-O-(dimethoxyltrityl)-2'-O-(hexyl-N-(folate)amino) uridine nucleoside The nucleoside product of Example 31 is treated as per the procedure of Example 5 to yield the product.

EXAMPLE 34

Preparation of 5'-O-(dim thoxytrityl)-2'-O-{hexyl-N-[2-methozy-6-chloro-9(Ω-amino-caproyl) acridine]amino}uridine.

6,9-Dichloro-2-methoxyacridine (Adlrich, 10 g, 36 mmol) and phenol (2.5 g) were placed together on a round-bottom flask with a stirring bar and to this 6-amino-hexanoic acid (9.3 g, 71 mmol) was added and the flask was heated to 100° (oil bath) for 2 hours. TLC (10% methanol in methylene chloride) showed complete disappearance of starting material. The reaction mixture was cooled and poured into 200 mL of methanol. The product isolates out as a yellow solid (about 10 g). This compound was then converted into its pentafluorophenol ester.

5'-O-(Dimethoxytrityl)-2'-(hexylamino)uridine (0.5 g, 0.78 mmol) is dissolved in anhydrous DMF (15 mL). 1-Hydroxybenzotriazole (0.16 grams, 1.17 mmol) and 2-methoxy-6-chloro-9-(Ω-caproyl-amino)acridine pentafluorophenyl ester (0.53 grams, 1.17 mmol) are added to the reaction mixture. The mixture is stirred under argon at room temperature for 2 h, after which it is concentrated in vacuo. Residual DMF is coevaporated with toluene. The residue is dissolved in dichloromethane (50 mL) and washed with an equal volume saturated NaHCO$_3$. The aqueous layer is washed with dichloromethane and the combined organic extracts washed with an equal volume saturated NaCl. The aqueous layer is washed with dichloromethane and the combined organic layers dried over MgSO$_4$ and concentrated. The residue is chromatographed on a silica gel column, eluting with a gradient of 50% ethyl acetate in hexanes to 100% ethyl acetate. The desired product elutes with 100% ethyl acetate.

EXAMPLE 35

Preparation of 5'-O-(dimethoxytrityl)-2'-O-{hexyl-N-[2-methoxy-6-chloro-9-(Ω-amino-caproyl) acridine]amino}uridine-3'-O-(2-cyanoethyl-N-N-diisopropyl)phospboramidite 5'-O-Dimethoxytrityl-2'-O-{hexyl-N-[2-methoxy-6-chloro-9-(w-amino-caproyl)acridine]amino}uridine (0.80 grams, 0.77 mmol) is dissolved in dry dichloromethane (20 mL). 2-Cyano-ethyl N,N,N',N'-tetraisopropylphosphorodiamidite (800 μL, 2.4 mmol) and diisopropylamine tetrazolide (0.090 grams, 0.52 mmol) are added to the mixture, which is stirred under argon for 20 hours. The reaction mixture is then concentrated in vacuo and the residue dissolved in dichloromethane (75 mL). The solution is washed with an equal volume of saturated $NaHCO_3$. The aqueous layer is washed with dichloromethane (20 mL) and the combined organic layers washed with an equal volume of saturated NaCl. The aqueous layer is washed with dichloromethane (20 mL) and the combined organic layers dried over $MgSO_4$ and concentrated. The residue is chromatographed on a silica gel column, eluting with a gradient of 50% ethyl acetate in hexanes to 92% ethyl acetate. The desired product elutes with 100% ethyl acetate.

EXAMPLE 36

Pr parati n of 5'-O-(dim thoxytrityl)-2'-O-{hexyl-N-[2-methoxy-6-chloro-9-(Ω-aminocaproyl)acridine]amino}uridine-3'-O-(succinyl aminopropyl) controlled pore glass Succinylated and capped controlled pore glass (0.3 grams) is added to 3 ml anhydrous pyridine in a 50 ml round-bottom flask. DEC (0.12 grams, 0.67 mmol), TEA (25 μl, distilled over $CaH_2$), DMAP (0.005 grams, 0.04 mmol) and 5'-O-dimethoxytrityl-2'-O-{hexyl-N-[2-methoxy-6-chloro-9-(Ω-aminocaproyl)acridine]amino}uridine (0.21 grams, 0.17 mmol) are added under argon and the mixture shaken mechanically for 19 hours. More nucleoside (0.025 grams) is added and the mixture shaken an additional 5.5 hours. Pentachlorophenol (0.045 grams, 0.17 mmol) is added and the mixture shaken 18 hours. CPG is filtered off and washed successively with dichloromethane, triethylamine, and dichloromethane. CPG is then dried under vacuum, suspended in 15 ml piperidine and shaken 15 minutes. CPG is filtered off, washed thoroughly with dichloromethane and again dried under vacuum. The extent of loading is determined by spectrophotometric assay of dimethoxytrityl cation in 0.3 M p-toluenesulfonic acid at 498 nm. to be approximately 27 μmol/g.

EXAMPLE 37

Preparation of 5'-O-(dimethoxytrityl)-2'-O-[(hexyl-N,N-dimethyl)amino]uridine

5'-O-(dimethoxytrityl)-2'-O-(hexylamino)uridine (0.19 grams, 0.29 mmol) is dissolved in 4 ml methanol. Sodium acetate pH 4.0 (2 ml), sodium cyanoborohydride (0.02 grams, 0.3 mmol) and 37% formaldehyde in water (300 μl) are added to the reaction mixture, which is stirred 2 hours, after which it is concentrated in vacuo. The residue is dissolved in dichloromethane (50 mL) and washed with an equal volume saturated $NaHCO_3$. The aqueous layer is washed with dichloromethane and the combined organic extracts washed with an equal volume saturated NaCl. The aqueous layer is washed with dichloromethane and the combined organic layers dried over $MgSO_4$ and concentrated. The residue is chromatographed on a silica gel column, eluting with a gradient of 50% ethyl acetate in hexanes to 100% ethyl acetate. The desired product (0.15 grams, 80%) elutes with 10% Methanol-90% ethyl acetate.

EXAMPLE 38

Oligonucleotides Having 3'-Alkylamino Group

3'-O-Hexyl-(N-phthalimido)-aminouridine-CPG, i.e. the 5'-O-dimethoxytrityl-3'-O-[hexyl-(Ω-N-phthalimido amino)]-uridine-2'-O-(succinyl-aminopropyl) controlled pore glass from Example 5, was used to synthesize the following oligonucleotides:

Oligomer 49: GAC U*

Oligomer 50: GCC TTT CGC GAC CCA ACA CU

Oligomer 51: GCC TTT CGC GAC CCA ACA CU* wherein "*" denotes the 3'-O hexylamino-modified nucleoside.

Standard commercial phosphoramidites were used with the synthesis cycle times specified by the manufacturer in a 380B ABI instrument (Applied Biosystems).

Oligomer 49 was used for structural proof of 3'-O-alkylamine-bearing oligonucleotides at the 3'-terminal end. It showed the expected three 31P NMR signals (–0.5 ppm, –0.25 ppm, –0,2 ppm) and seven lines in the trace aromatic base region in 1H NMR its spectrum.

Oligomer 51 was used to demonstrate the nuclease resistance offered by this the alkylamino group and also for further conjugation. The oligomer was treated with pyrenebutyric acid-N-hydroxy succinimide ester in 0.2 M $NaHCO_3$ buffer/DMF. The product, Conjugate 1, was purified by HPLC and size exclusion methods. HPLC retention times (eluting with a gradient of 5% $CH_3CN$ for 10 minutes then 5%–40% $CH_3CN$ for 50 minutes) were as follows:

|  | Retention Time (min.) |
| --- | --- |
| Oligomer 50 | 25.99 |
| Oligomer 51 | 25.91 |
| Conjugate 1 | 49.35 |

The nuclease stability of oligomer 51 and the conjugate were tested against Oligomer 50 in HeLa cytoplasmic/nuclear extracts. The cell extract was diluted 1.4 times. The final concentration of oligonucleotide was 20 μM. The half lives of the oligonucleotides were as follows:

|  | t½ (hours) |
| --- | --- |
| Oligomer 50 | 1.0 |
| Oligomer 51 | 3.5 |
| Conjugate 1 | 3.6 |

The half life of phosphodiester Oligomer 50 increased 3–4 times by simple modification at the 3'-end with the hexylamino group, by itself, or by further conjugation.

EXAMPLE 39

Oligonucleotides Having 2'-O-Alkylamino Group

A. The phosphoramidite from Example 4, 5'-O-(dimethoxytrityl)-2'-O-[hexyl-(Ω-N-phthalimido)amino]-uridine-3'-O-[(2-cyanoethyl)-N,N-diisopropyl] phosphoramidite was made as a 0.2 M solution in anhydrous $CH_3CN$ and used to synthesize the following oligonucleotides in an ABI DNA synthesizer, model 380 B. During the modified amidite coupling, the reaction time was increased to 10 minutes. A coupling efficiency of approximately 90% was observed. After deprotection with concentrated ammonium hydroxide (55° C., 16 hours) the oligonucleotides were purified by reverse phase HPLC and desalting column (Sephadex G-25).

Oligomer 52 (SEQ ID NO:14): GCGTGU*CTGCG

Oligomer 53: GAU*CT

B. GCGTGTU'CTGCG where U' is 2'-O-[hexyl-N-(1-pyrenepropyl-carbonyl)amino uridine, Conjugate 2 (Oligomer 52—pyrene butyrate conjugate).

To 20 O.D. of Oligomer 52 in 200 μL of 0.2 M NaHCO$_3$ buffer, 5 ml of pyrene-butyric acid-N-hydroxy succinimide ester in an Eppendorf tube was added followed by 200 μL of DMF. The tube was shaken overnight. The reaction was purified by size exclusion and HPLC to yield 18 O.D. of product.

C. GCGTGTU"CTGCG where U" is 2'-O-[6-bromoacetymidohex-1yl]-uridine, Conjugate 3 (Oligomer 52—bromoacetate conjugate).

To 12 O.D. of Oligomer 52 in 100 μL of 0.2 M NaHCO$_3$ buffer, 2 mg bromoacetic acid-NHS ester (N-hydroxy succinimidyl bromoacetate) was added. After leaving the reaction to stand overnight, it was purified by size exclusion and HPLC to yield 7.5 O.D. of product.

D. GCGTGTU^ACTGCG wh re U^ is 2'-O-[hexyl-N-(polyethylene glycol)-propionoyl]amino uridin, C njugat 4 (Oligomer 52—PEG conjugate).

To 24 O.D. of Oligomer 52 in 200 μL of 0.2 M NaHCO$_3$ buffer, 20 mg of Polyethylene glycol propionic acid-N-hydroxy succinimide ester was added. The reaction was mechanically shaken overnight and purified by Sephadex G-25 size exclusion and chromatography to yield 22 O.D. of product.

HPLC retention times (eluting with a gradient of 5% CH$_3$CN for 10 minutes then 5%–40% CH$_3$CN for 50 minutes in a C-18 Delta-Pak reverse phase column) were as follows:

|  | Retention Time (min.) |
| --- | --- |
| Oligomer 52 | 24.05 |
| Conjugate 2 | 40.80 |
| Conjugate 3 | 26.04 |
| Conjugate 4 | 55.58 |

Changes in $T_m$ due to pyrene conjugation were evaluated against both DNA and RNA. $T_m$ was measured in 100 mM Na$^+$, 10 nM phosphate, 0.1 mM EDTA, pH 7 at 4 μM strand concentration. The results were as follows:

|  | $T_m$ v. DNA (° C.) | $T_m$ V. RNA (° C.) |
| --- | --- | --- |
| Oligomer 52 | 50.9 | 55.5 |
| Conjugate 2 | 55.3 | 55.5 |
|  | (4.4) | (0.0) |

The values in parentheses are changes in $T_m$ compared to amino linker in oligomer 52 as a control.

EXAMPLE 40

Oligonucleotide synthesis using 2'-O-hexylamino (pyrene-butyrate)uridine phosphoramidite The amidite 5'-O-(dimethoxytrityl)-2'-O-[hexyl-N-(1-pyrene propyl carbonyl)amino]uridine-31-O-(2-cyanoethyl-N,N-diisopropyl)phosphoramidite (0.2 M in anhydrous acetonitrile) was used to synthesize the following oligomers, both for NMR studies:

Oligomer 54: GAU*CT

Oligomer 55: GCC GU*G TCG (U*=2'-O-modified phosphoramidite)

These oligomers were purified trityl-on reverse-phase HPLC, detritylated in 80% acetic acid for one hour and then repurified by RP-HPLC and desalted by size-exclusion chromatography. NMR analysis showed the presence of pyrene peaks.

EXAMPLE 41

Oligonucleotide synthesis using 2'-O-hexylamino (dinitrophenyl)uridine phosphoramidite The amidite5'-O-(dimethoxytrityl)-2'-O-[hexyl-N-(2,4-dinitrophenyl)amino]uridine-3'-O-(2-cyanoethyl-N,N,-diisopropyl)phosphoramidite (0.18 M in anhydrous acetonitrile) was used to synthesize oligonucleotides, Oligomers 56 to 63. All are analogues of an ICAM antisense sequence. These oligomers were purified trityl-on by RP-HPLC (Waters Delta-Pak C$_{18}$ column, 300 Å, 7.8 mm×30 cm, linear 50-min gradient of 5–60% acetonitrile in 0.05 M TEAA pH 7.3), detritylated in 80% acetic acid for one hour and then purified by RP-HPLC and desalted by size-exclusion chromatography. Data are summarized below:

|  | Backbone | Total (O.D.) | Retention Time (min) |
| --- | --- | --- | --- |
| Oligomer 56: GAU CT | P = O | 40 | 39.16 |
| Oligomer 57: (SEQ ID NO:15) U*GG GAG CCA TAG CGA GGC# | P = S | 64 | 39.19 |
| Oligomer 58: U*GG GAG CCA TAG CGA GGC | P = S | 45 | 39.21 |
| Oligomer 59: U*GG GAG CCA TAG CGA GGC | P = O | 60 | 37.68 |
| Oligomer 60: U*GG GAG CCA U*AG CGA GGC | P = O | 69 | 38.58 |
| Oligomer 61: TGG GAG CCA U*AG CGA GGC (SEQ ID NO:16) | P = O | 86 | 32.38 |
| Oligomer 62: U*<u>CT GAG TAG CAG AGG AGC TC</u># (SEQ ID NO:17) | P = O | 34 | 35.76 |
| Oligomer 63: U*GG GAG CCA U*AG CGA GGC# | P = S | 72 | 43.37 |

= Non-nucleoside 6-carbon amino linker (Glen Research) and Bold indicates nucleotides having 2'-O-methyl substitutions

EXAMPLE 42

Oligonucleotide synthesis using 2'-O-[hexylamino-(cholesterol)]uridine phosphoramidite The amidite 5'-O-dimethoxytrityl-2'-O-[hexyl-N-(3-oxycarbonyl-cholesteryl)amino]uridine-3'-O-[2-cyanoethyl-N,N,-diisopropyl]-phosphoramidite (0.2 M in anhydrous acetonitrile/dichloromethane 2:1 v/v) was used to synthesize Oligomers 67–74. These oligomers are purified trityl-on by reverse-phase HPLC (Waters Delta-Pak C$_{18}$, 300 Å, 7.8 mm×30 cm, linear 55-min gradient of 5–80% acetonitrile in 0.05 M TEAA pH 7.3), detritylated in 80% acetic acid for one hour and then repurified by RP-HPLC and desalted by size-exclusion chromatography. Data are summarized below:

| | Backbone | Target | Retention Time (min) |
|---|---|---|---|
| Oligomer 67:<br>GAU*CT | P = O | NMR | 52.73 |
| Oligomer 68:<br>U*GG GAG CCA TAG CGA GGC | P = O | ICAM | 49.64 |
| Oligomer 69:<br>U*GC CCA AGC TGG CAT CCG TCA<br>(SEQ ID NO:18) | P = S | ICAM | 51.98 |
| Oligomer 70:<br>U*GC GTT TGC TCT TCT TCT TGC G<br>(SEQ ID NO:19) | P = S | CMV | 52.57 |
| Oligomer 71:<br>U*GC ATC CCC CAG GCC ACC AT<br>(SEQ ID NO:20) | P = S | mseICAM | 53.24 |
| Oligomer 72:<br>U*CC CGC CTG TGA CAT GCA TT<br>(SEQ ID NO:21) | P = S | Raf | 53.95 |
| Oligomer 73:<br>GU*T CTC GCT GGT GAG TTT CA<br>(SEQ ID NO:22) | P = S | PKCa | 51.04 |
| Oligomer 74:<br>Fl-UU*GG GAG CCA TAG CGA GGC<br>(SEQ ID NO:23) | P = S | ICAM | 52.75 |

Fl-U = U 2'-modified with fluorescein (see Example 42).

EXAMPLE 42

Synthesis of oligonucleotides using 2'-O-[hexylamino-(fluorescein)] amidite

The amidite 5'-O-dimethoxytrityl-2'-O-[hexyl-N-(5-thiocarbonyl-3,6-dipivolyl fluorescein)amino]uridine-3'-O-(cyanoethyl-N,N-diisopropyl phosphoramidite) (0.2 M in anhydrous acetonitrile) was used to synthesize Oligomer 74 (above) and Oligomers 75–82 on a 1×10$^5$ (Oligomer 75) or 1×10$^2$ (remaining oligomers) μmol scale. These oligomers are purified trityl-on by reverse phase HPLC (Waters Delta-Pak C$_{18}$, 300 Å, 7.8 mm×30 cm, linear gradient of acetonitrile in 0.05 M TEAA pH 7.3), detritylated in 80% acetic acid for one hour and then repurified by RP-HPLC and desalted by size-exclusion chromatography.

| | Backbone | Target |
|---|---|---|
| Oligomer 75:<br>GAU*CT | P = O | NMR |
| Oligomer 76:<br>U*GG GAG CCA TAG CGA GGC | P = O | ICAM |
| Oligomer 77:<br>U*GC CCA AGC TGG CAT CCG TCA | P = S | ICAM |
| Oligomer 78:<br>U*GC CCA AGC TGG CAT CCG TCA# | P = S | ICAM |
| Oligomer 79:<br>U*GC GTT TGC TCT TCT TCT TGC G | P = S | CMV |
| Oligomer 80:<br>U*GC ATC CCC CAG GCC ACC AT | P = S | mseICAM |
| Oligomer 81:<br>U*GC ATC CCC CAG GCC ACC A<br>(U-CPG)<br>(U-CPG) = 2'-O-hexylphthalimido U 6 | P = S | mseICAM |
| Oligomer 82:<br>GU*T CTC GCT GGT GAG TTT CA | P = S | PKC |

Where U* is U modified with fluorescein.

---

What is claimed is:

1. A compound comprising a plurality of linked nucleosides, wherein:
   each nucleoside includes a pentofuranosyl sugar portion and a base portion; and
   at least one of said nucleosides bears at a 2'-O-position, a 3'-O-position, or a 5'-O-position of said pentofuranosyl sugar a terminal substituent having formula:

—$R_A$—N($R_{1a}$)($R_{1b}$)

where:
   $R_A$ is alkyl having from 1 to about 10 carbon atoms or (CH$_2$—CH$_2$—Q)$_x$;
   $R_{1a}$ and $R_{1b}$, independently, are H, $R_2$, or an amine protecting group or have formula C(X)—$R_2$, C(X)—$R_A$—$R_2$, C(X)—Q—$R_A$—$R_2$, C(X)—Q—$R_2$; and
   $R_2$ is a folate, a steroid molecule, a reporter molecule, a lipophilic molecule, a reporter enzyme, a peptide, a protein, or has formula —Q—(CH$_2$CH$_2$—Q—)$_x$—$R_3$;
   X is O or S;
   each Q is, independently, is NH, O, or S;
   x is about 1 to about 50;
   $R_3$ is H, $R_A$, C(O)OH, C(O)O$R_A$, C(O)$R_4$, $R_A$—N$_3$, or $R_A$—NH$_2$;
   $R_4$ is Cl, Br, I, SO$_2$$R_5$ or has structure:

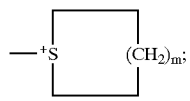

m is 2 to 7; and
   $R_5$ alkyl having 1 to about 10 carbon atoms.

2. The compound of claim 1 wherein more than one of said nucleosides bear said substituent at a 2'-O-position, a 3'-O-position, or a 5'-O-position.

3. The compound of claim 1 wherein $R_A$ is (CH$_2$)$_n$ where n is an integer from 1 to about 10.

4. The compound of claim 3 wherein n is 6.

5. The compound of claim 1 wherein said $R_{1a}$ is H and $R_{1b}$, together, are phthalimido.

6. The compound of claim 1 wherein $R_{1a}$ is H and $R_{1b}$ is C(O)—(CH$_2$)$_n$—$R_2$ where n is an integer from 1 to about 10.

7. The compound of claim 1 wherein $R_{1a}$ is H and $R_{1b}$ is $R_2$.

8. The compound of claim 1 wherein $R_{1a}$ is H and $R_{1b}$ is C(O)—O—$R_2$.

9. The compound of claim 1 wherein $R_{1a}$ and $R_{1b}$ both are alkyl.

10. The compound of claim 1 wherein $R_{1a}$ is H and $R_{1b}$ is C(O)—(CH$_2$)$_n$—$R_2$ where n is an integer from 1 to about 10.

11. The compound of claim 10 wherein $R_2$ has formula —(CH$_2$)$_5$—NH—.

12. The compound of claim 1 wherein $R_{1a}$ is H and $R_{1b}$ is C(S)—NH—$R_2$.

13. The compound of claim 1 wherein $R_2$ includes pyrene, fluorescein, dinitrophenyl, cholesterol, acridine.

14. The compound of claim 1 wherein $R_{1a}$ is H and $R_{1b}$ is C(O)—$R_2$.

15. The compound of claim 14 wherein $R_2$ has formula —O—(CH$_2$CH$_2$—O—)$_x$—$R_3$.

16. A nucleoside comprising a pentofuranosyl sugar portion and a base portion, wherein said nucleoside bears at a 2'-O-position of said pentofuranosyl sugar, a 3'-O-position, or a 5'-O-position a substituent having the formula:

—$R_A$—N($R_{1a}$)($R_{1b}$)

where:
   $R_A$ is alkyl having from 1 to about 10 carbon atoms;
   $R_{1a}$ and $R_{1b}$, independently, are H, $R_2$, or an amine protecting group or have formula C(X)—$R_2$, C(X)—$R_A$—$R_2$, C(X)—Q—$R_A$—$R_2$, C(X)—Q—$R_2$; and
   $R_2$ is a steroid molecule, a reporter molecule, a lipophilic molecule, a reporter enzyme, a peptide, a protein, or has formula —Q—(CH$_2$CH$_2$—Q—)$_x$—$R_3$;
   X is O or S;
   each Q is, independently, is NH, O, or S;
   x is about 1 to about 50;
   $R_3$ is H, $R_A$, C(O)OH, C(O)O$R_A$, C(O)$R_4$, $R_A$—N$_3$, or $R_A$—NH$_2$; and
   $R_4$ is Cl, Br, I, SO$_2$$R_5$ or has structure:

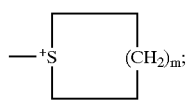

m is 2 to 7; and
   $R_5$ alkyl having 1 to about 10 carbon atoms.

17. The nucleoside of claim 16 wherein $R_A$ is (CH$_2$)$_n$ where n is an integer from 1 to about 10.

18. The nucleoside of claim 16 wherein n is 6.

19. The nucleoside of claim 16 wherein said $R_{1a}$ is H and $R_{1b}$, together are phthalamido.

20. The nucleoside of claim 16 wherein $R_{1a}$ is H and $R_{1b}$ is C(O)—(CH$_2$)$_n$—$R_2$ where n is an integer from 1 to about 10.

21. The nucleoside of claim 16 wherein $R_{1a}$ is H and $R_{1b}$ is $R_2$.

22. The nucleoside of claim 16 wherein $R_{1a}$ is H and $R_{1b}$ is C(O)—O—$R_2$.

23. The nucleoside of claim 16 wherein $R_{1a}$ and $R_{1b}$ both are alkyl.

24. The nucleoside of claim 16 wherein $R_{1a}$ is H and $R_{1b}$ is C(O)—(CH$_2$)$_n$—$R_2$ where n is an integer from 1 to about 10.

25. The nucleoside of claim 24 wherein $R_2$ has formula —$(CH_2)_5$—NH—.

26. The nucleoside of claim 16 wherein $R_{1a}$ is H and $R_{1b}$ is C(S)—NH—$R_2$.

27. The nucleoside of claim 16 wherein $R_2$ includes pyrene, fluorescein, dinitrophenyl, cholesterol, acridine.

28. The nucleoside of claim 16 wherein $R_{1a}$ is H and $R_{1b}$ is C(O)—$R_2$.

29. The nucleoside of claim 28 wherein $R_2$ has formula —O—$(CH_2CH_2$—O—$)_x$—$R_3$.

* * * * *

UNITED STATES PATENT AND TRADEMARK OFFICE
CERTIFICATE OF CORRECTION

PATENT NO. : 6,783,931 B1  
DATED : August 31, 2004  
INVENTOR(S) : Cook et al.

Page 1 of 1

It is certified that error appears in the above-identified patent and that said Letters Patent is hereby corrected as shown below:

<u>Title page,</u>
Item [56], References Cited, OTHER PUBLICATIONS,
"Englisch" reference, insert -- Int. -- between "Chem." and "Ed.";

<u>Column 44,</u>
Line 19, delete "of said pentofuranosyl sugar";
Line 20, insert -- of said pentofuranosyl sugar -- between "5'-O-position" and "a subtituent".

Signed and Sealed this

Sixteenth Day of May, 2006

JON W. DUDAS
*Director of the United States Patent and Trademark Office*

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GGCTGACTGC G                                  11

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear

```
        (ii) MOLECULE TYPE: DNA (genomic)

(xi) SEQUENCE DESCRIPTION: SEQ ID NO:2:

CTGTCTCCAT CCTCTTCACT                                              20

(2) INFORMATION FOR SEQ ID NO:3:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:3:

TTGCTTCCAT CTTCCTCGTC                                              20

(2) INFORMATION FOR SEQ ID NO:4:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:4:

TGGGAGCCAT AGCGAGGC                                                18

(2) INFORMATION FOR SEQ ID NO:5:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:5:

CTGTCTCCAT CCTCTTCACT                                              20

(2) INFORMATION FOR SEQ ID NO:6:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:6:

TCCAGGTGTC CGCATC                                                  16

(2) INFORMATION FOR SEQ ID NO:7:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:7:
```

GGACCGGAAG GTACGAG                                                     17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CCTGGCCTTC CATGCTC                                                     17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:9:

CCUGGCCUUC CAUGCUC                                                     17

(2) INFORMATION FOR SEQ ID NO:10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CCCAGGCUCA GA                                                          12

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GAGCUCCCAG GC                                                          12

(2) INFORMATION FOR SEQ ID NO:12:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CAUGCUGCAGCC                                                           12

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GCCTTTCGCG ACCCAACACU                                                20

(2) INFORMATION FOR SEQ ID NO:14:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GCGTGUCTGC G                                                                         11

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

UGGGAGCCAT AGCGAGGC                                                   18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TGGGAGCCAU AGCGAGGC                                                   18

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

UCTGAGTAGC AGAGGAGCTC                                               20

(2) INFORMATION FOR SEQ ID NO:18:

(i) SEQUENCE CHARACTERISTICS:
        (A) LENGTH: 21 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

UGCCCAAGCT GGCATCCGTC A                                              21

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

UGCGTTTGCT CTTCTTCTTG CG                                             22

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

UGCATCCCCC AGGCCACCAT                                                20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

UCCCGCCTGT GACATGCATT                                                20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GUTCTCGCTG GTGAGTTTCA                                                20

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:23:

UUGGGAGCCA TAGCGAGGC                                                    19